United States Patent [19]
Backman et al.

[11] Patent Number: 5,516,663
[45] Date of Patent: May 14, 1996

[54] LIGASE CHAIN REACTION WITH ENDONUCLEASE IV CORRECTION AND CONTAMINATION CONTROL

[75] Inventors: Keith C. Backman, Bedford, Mass.; John J. Carrino, Gurnee, Ill.; George H. Shimer, Boston; Robert R. Yocum, Lexington, Mass.

[73] Assignee: Abbott Laboratories, Abbott Park, Ill.

[21] Appl. No.: 49,061

[22] Filed: Apr. 19, 1993

Related U.S. Application Data

[63] Continuation-in-part of Ser. No. 634,771, Jan. 9, 1991, abandoned, Ser. No. 722,798, Jun. 28, 1991, Pat. No. 5,427,930, Ser. No. 869,306, Apr. 16, 1992, abandoned, Ser. No. 925,402, Aug. 3, 1992, abandoned, and Ser. No. 826,932, Jan. 21, 1992, abandoned, said Ser. No. 634,771, is a continuation-in-part of Ser. No. 470,674, Jan. 31, 1990, abandoned, said Ser. No. 869,306, is a continuation of Ser. No. 860,861, Mar. 31, 1992, abandoned.

[51] Int. Cl.$^6$ .............................. C12P 19/34; C07H 21/04
[52] U.S. Cl. .............................. 435/91.2; 435/6; 435/91.1; 436/501; 536/22.1; 536/23.1; 536/24.1; 536/24.3; 536/24.31; 536/24.32; 536/24.33; 935/77; 935/78
[58] Field of Search .............................. 435/6, 91.1, 91.2; 436/501; 935/77, 78; 536/22.1, 23.1, 24.1, 24.3–24.33

[56] References Cited

U.S. PATENT DOCUMENTS 4,851,331  7/1989  Vary et al. .................................. 435/6

FOREIGN PATENT DOCUMENTS 246864   11/1987  European Pat. Off. .
320308   12/1988  European Pat. Off. .
0439182   1/1991   European Pat. Off. .
496483   1/1992   European Pat. Off. .
WO91/17270  4/1991  WIPO .

OTHER PUBLICATIONS

Levin, et al., "Metalloenzymes in DNA Repair", J. Biol. Chem. 266(34):22893–22898 (1991).

Johnson and Demple, "Yeast DNA Diesterase for 3' Fragments of Deoxyribose: Purification and Physical Properties of a Repair Enzyme for Oxidative DNA Damage", J. Biol. Chem. 263(34):18009–18016 (1988).

Siwek, et al., "The Relative Importance of Escherichia coli Exonuclease III and Endonuclease IV for the Hydrolysis of 3'-Phosphoglycolate Ends in Polydeoxynucleotides", Nucl. Acids Res. 16:5031–5038 (1988).

Doetsch and Cunningham, "The Enzymology of Apurinic/Apyrimidinic Endonucleases", Mutation Research, 236:173–201 (1990).

Brutlag et al., J. Biol. Chem., 247, (1), (Jan., 1972), pp. 241–248.

Bailly et al., Biochem. J., 259, (1989), pp. 761–768.

Primary Examiner—W. Gary Jones
Assistant Examiner—Ardin H. Marschel
Attorney, Agent, or Firm—Thomas D. Brainard; Paul D. Yasger

[57] ABSTRACT

The present invention involves methods of improving the Ligase Chain Reaction (LCR™) amplification schemes by modifying at least one probe end so that the probability of the probe contributing to spurious ligation and signal development is greatly reduced. Only after specific hybridization of the modified probe with true target are the modified ends "corrected" by endonuclease IV in a target dependent fashion to allow participation of the probe in the enzymatic ligation reaction. Specific modifications include 3' phosphate blocking groups and nucleic acid overhangs containing an abasic site at the point of ligation. Further embodiments include probes modified to contain ribonucleotide moieties which, after amplification, can be cleaved by RNase to destroy the amplification products and reduce the risk of contamination.

40 Claims, 4 Drawing Sheets

SEQUENCE LISTING ( 1 ) GENERAL INFORMATION:

( i i i ) NUMBER OF SEQUENCES: 38

( 2 ) INFORMATION FOR SEQ ID NO: 1:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 1:

TTGTCGAGCA CCTTGAATAA                                           2 0

( 2 ) INFORMATION FOR SEQ ID NO: 2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: 3'end phosphorylated
        ( B ) LOCATION: 20

( x i ) SEQUENCE DESCRIPTION: SEQ ID NO: 2:

TTGTCGAGCA CCTTGAATAA                                                           20

( 2 ) INFORMATION FOR SEQ ID NO: 3:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: N represents an abasic site
        ( B ) LOCATION: 21

( x i ) SEQUENCE DESCRIPTION: SEQ ID NO: 3:

TTGTCGAGCA CCTTGAATAA NT                                                        22

( 2 ) INFORMATION FOR SEQ ID NO: 4:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: N represents an abasic site
        ( B ) LOCATION: 21

( x i ) SEQUENCE DESCRIPTION: SEQ ID NO: 4:

TTGTCGAGCA CCTTGAATAA NTAA                                                      24

( 2 ) INFORMATION FOR SEQ ID NO: 5:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: N represents an abasic site
        ( B ) LOCATION: 21

( x i ) SEQUENCE DESCRIPTION: SEQ ID NO: 5:

TTGTCGAGCA CCTTGAATAA NTAATG                                                    26

( 2 ) INFORMATION FOR SEQ ID NO: 6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 6:

TTAATGGCTT CGATTGGGCT                                                           20

( 2 ) INFORMATION FOR SEQ ID NO: 7:

( i ) SEQUENCE CHARACTERISTICS:

(A) LENGTH: 20
            (B) TYPE: nucleic acid
            (C) STRANDEDNESS: single
            (D) TOPOLOGY: linear (ii) MOLECULE TYPE: Other nucleic acid (synthetic DNA)

(xi) SEQUENCE DESCRIPTION: SEQ ID NO: 7:

TTATTCAAGG TGCTCGACAA 20

(2) INFORMATION FOR SEQ ID NO: 8:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: Other nucleic acid (synthetic DNA)

(xi) SEQUENCE DESCRIPTION: SEQ ID NO: 8:

ATTCAAGGTG CTCGACAA 18

(2) INFORMATION FOR SEQ ID NO: 9:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: Other nucleic acid (synthetic DNA)

(ix) FEATURE:
            (A) NAME/KEY: 3'end phosphorylated
            (B) LOCATION: 22

(xi) SEQUENCE DESCRIPTION: SEQ ID NO: 9:

AGCCCAATCG AAGCCATTAA TT 22

(2) INFORMATION FOR SEQ ID NO: 10:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: Other nucleic acid (synthetic DNA)

(ix) FEATURE:
            (A) NAME/KEY: 3'end phosphorylated
            (B) LOCATION: 20

(xi) SEQUENCE DESCRIPTION: SEQ ID NO: 10:

AGCCCAATCG AAGCCATTAA 20

(2) INFORMATION FOR SEQ ID NO: 11:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: Other nucleic acid (synthetic DNA)

(xi) SEQUENCE DESCRIPTION: SEQ ID NO: 11:

AGCCCAATCG AAGCCATTAA 20

( 2 ) INFORMATION FOR SEQ ID NO: 12:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: N represents an abasic site
        ( B ) LOCATION: 23

( x i ) SEQUENCE DESCRIPTION: SEQ ID NO: 12:

AGCCCAATCG AAGCCATTAA TTNT        24

( 2 ) INFORMATION FOR SEQ ID NO: 13:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: N represents an abasic site
        ( B ) LOCATION: 23

( x i ) SEQUENCE DESCRIPTION: SEQ ID NO: 13:

AGCCCAATCG AAGCCATTAA TTNTTC        26

( 2 ) INFORMATION FOR SEQ ID NO: 14:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: N represents an abasic site
        ( B ) LOCATION: 23

( x i ) SEQUENCE DESCRIPTION: SEQ ID NO: 14:

AGCCCAATCG AAGCCATTAA TTNTTCAA        28

( 2 ) INFORMATION FOR SEQ ID NO: 15:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 15:

CCGATTGCAA TGTAATATCG ACGTC        25

( 2 ) INFORMATION FOR SEQ ID NO: 16:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear (i i) MOLECULE TYPE: Other nucleic acid (synthetic DNA)

(i x) FEATURE:
    (A) NAME/KEY: N represents an abasic site
    (B) LOCATION: 26

(x i) SEQUENCE DESCRIPTION: SEQ ID NO: 16:

```
CCGATTGCAA TGTAATATCG ACGTCNTCGG C                    31
```

(2) INFORMATION FOR SEQ ID NO: 17:

(i) SEQUENCE CHARACTERISTICS:
        (A) LENGTH: 21
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 17:

```
GTCGGGCAAA TAATTCGCCA C                               21
```

(2) INFORMATION FOR SEQ ID NO: 18:

(i) SEQUENCE CHARACTERISTICS:
        (A) LENGTH: 24
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 18:

```
GACGTCGATA TTACATTGCA ATCG                            24
```

(2) INFORMATION FOR SEQ ID NO: 19:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 19:

```
CGTCGATATT ACATTGCAAT CG                              22
```

(2) INFORMATION FOR SEQ ID NO: 20:

(i) SEQUENCE CHARACTERISTICS:
        (A) LENGTH: 19
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 20:

```
GGCGAATTAT TTGCCCGAC                                  19
```

(2) INFORMATION FOR SEQ ID NO: 21:

(i) SEQUENCE CHARACTERISTICS:
        (A) LENGTH: 21
        (B) TYPE: nucleic acid
        (C) STRANDEDNESS: single
        (D) TOPOLOGY: linear (i i) MOLECULE TYPE: Other nucleic acid (synthetic DNA)

( x i ) SEQUENCE DESCRIPTION: SEQ ID NO: 21:

GGCGAATTAT TTGCCCGACG A                                                          21

( 2 ) INFORMATION FOR SEQ ID NO: 22:

( i ) SEQUENCE CHARACTERISTICS:
        ( A ) LENGTH: 40
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 22:

TTGTCGAGCA CCTTGAATAA TTAATGGCTT CGATTGGGCT                                      40

( 2 ) INFORMATION FOR SEQ ID NO: 23:

( i ) SEQUENCE CHARACTERISTICS:
        ( A ) LENGTH: 40
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 23:

AGCCCAATCG AAGCCATTAA TTATTCAAGG TGCTCGACAA                                      40

( 2 ) INFORMATION FOR SEQ ID NO: 24:

( i ) SEQUENCE CHARACTERISTICS:
        ( A ) LENGTH: 45
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: N represents an abasic site
        ( B ) LOCATION: 36

( x i ) SEQUENCE DESCRIPTION: SEQ ID NO: 24:

AAAAAAGCC GGATCCGTAC ACAACGGATC CGGCTNTTTT TGGGG                                 45

( 2 ) INFORMATION FOR SEQ ID NO: 25:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: adenosine ribonucleotide
        ( B ) LOCATION: 20

( x i ) SEQUENCE DESCRIPTION: SEQ ID NO: 25:

TTGTCGAGCA CCTTGAATAA                                                            20

( 2 ) INFORMATION FOR SEQ ID NO: 26:

( i ) SEQUENCE CHARACTERISTICS:
        ( A ) LENGTH: 20
        ( B ) TYPE: nucleic acid
        ( C ) STRANDEDNESS: single ( D ) TOPOLOGY: linear ( i i ) MOLECULE TYPE: Other nucleic acid (synthetic)

( i x ) FEATURE:
                ( A ) NAME/KEY: adenosine ribonucleotide
                ( B ) LOCATION: 20

( i x ) FEATURE:
                ( A ) NAME/KEY: 3'end phosphorylated
                ( B ) LOCATION: 20

( x i ) SEQUENCE DESCRIPTION: SEQ ID NO: 26:

TTGTCGAGCA CCTTGAATAA                                                        20

( 2 ) INFORMATION FOR SEQ ID NO: 27:

( i ) SEQUENCE CHARACTERISTICS:
                ( A ) LENGTH: 20
                ( B ) TYPE: nucleic acid
                ( C ) STRANDEDNESS: single
                ( D ) TOPOLOGY: linear ( i i ) MOLECULE TYPE: Other nucleic acid (synthetic DNA)

( i x ) FEATURE:
                ( A ) NAME/KEY: adenosine ribonucleotide
                ( B ) LOCATION: 20

( x i ) SEQUENCE DESCRIPTION: SEQ ID NO: 27:

AGCCCAATCG AAGCCATTAA                                                        20

( 2 ) INFORMATION FOR SEQ ID NO: 28:

( i ) SEQUENCE CHARACTERISTICS:
                ( A ) LENGTH: 20
                ( B ) TYPE: nucleic acid
                ( C ) STRANDEDNESS: single
                ( D ) TOPOLOGY: linear ( i i ) MOLECULE TYPE: Other nucleic acid (synthetic DNA)

( i x ) FEATURE:
                ( A ) NAME/KEY: adenosine ribonucleotide
                ( B ) LOCATION: 20

( i x ) FEATURE:
                ( A ) NAME/KEY: 3'end phosphorylated
                ( B ) LOCATION: 20

( x i ) SEQUENCE DESCRIPTION: SEQ ID NO: 28:

AGCCCAATCG AAGCCATTAA                                                        20

( 2 ) INFORMATION FOR SEQ ID NO: 29:

( i ) SEQUENCE CHARACTERISTICS:
                ( A ) LENGTH: 18
                ( B ) TYPE: nucleic acid
                ( C ) STRANDEDNESS: single
                ( D ) TOPOLOGY: linear ( i i ) MOLECULE TYPE: Other nucleic acid (synthetic DNA)

( i x ) FEATURE:
                ( A ) NAME/KEY: 3'end phosphorylated
                ( B ) LOCATION: 18

( x i ) SEQUENCE DESCRIPTION: SEQ ID NO: 29:

AATTCGAGCT CGGTACCC                                                          18

( 2 ) INFORMATION FOR SEQ ID NO: 30:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: Other nucleic acid (synthetic DNA)

( i x ) FEATURE:
    ( A ) NAME/KEY: N represents an abasic site
    ( B ) LOCATION: 19

( x i ) SEQUENCE DESCRIPTION: SEQ ID NO: 30:

AATTCGAGCT CGGTACCCNG                    20

( 2 ) INFORMATION FOR SEQ ID NO: 31:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 31:

GGGGATCCTC TAGAGTCGAC CTGCA              25

( 2 ) INFORMATION FOR SEQ ID NO: 32:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 32:

GGGTACCGAG CTCG                          14

( 2 ) INFORMATION FOR SEQ ID NO: 33:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: 3'end phosphorylated
        ( B ) LOCATION: 20

( x i ) SEQUENCE DESCRIPTION: SEQ ID NO: 33:

GTCGACTCTA GAGGATCCCC                    20

( 2 ) INFORMATION FOR SEQ ID NO: 34:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: N represents an abasic site
        ( B ) LOCATION: 21

( x i ) SEQUENCE DESCRIPTION: SEQ ID NO: 34:

GTCGACTCTA GAGGATCCCC NG 22

( 2 ) INFORMATION FOR SEQ ID NO: 35:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: 3'end phosphorylated
        ( B ) LOCATION: 22

( x i ) SEQUENCE DESCRIPTION: SEQ ID NO: 35:

GATACTTCGC ATCATGTGTT CC 22

( 2 ) INFORMATION FOR SEQ ID NO: 36:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 36:

GGAGTTTCTT TGTCCTCCTA TAACG 25

( 2 ) INFORMATION FOR SEQ ID NO: 37:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 37:

GGAACACATG ATGCGAAGTA TC 22

( 2 ) INFORMATION FOR SEQ ID NO: 38:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i x ) FEATURE:
        ( A ) NAME/KEY: 3'end phosphorylated
        ( B ) LOCATION: 25

( x i ) SEQUENCE DESCRIPTION: SEQ ID NO: 38:

CGTTATAGGA GGACAAAGAA ACTCC 25

LIGASE CHAIN REACTION WITH ENDONUCLEASE IV CORRECTION AND CONTAMINATION CONTROL

This application is a continuation-in-part of each of the following U.S. applications:

Ser. No.07/634,771, filed Jan. 9, 1991, abandoned, which is a continuation-in-part of application Ser. No. 07/470,674, filed Jan. 31, 1990, now abandoned;

Ser. No. 07/722,798, filed Jun. 28, 1991, issued at U.S. Pat. No. 5,427,930;

Ser. No. 07/869,306, filed Apr. 16, 1992, abandoned, which is a continuation of Ser. No. 07/860,861, filed Mar. 31, 1992, now abandoned;

Ser. No. 07/925,402, filed Aug. 3, 1992, abandoned; and

Ser. No. 07/826,932, filed January 21, 1992, abandoned.

The first two mentioned applications form the basis of EP-A-0 439 182, published on Jul. 31, 1991. The entire disclosure of each of the above-mentioned applications is incorporated herein by reference.

BACKGROUND

This invention relates to methods of amplifying target nucleic acids and, particularly, to methods of performing ligase chain reaction amplifications wherein at least one of the probes is reversibly modified at the ligation site so that it is not a substrate for the enzyme catalyzed ligation. Exemplary modifications include chemical blockage of reactant groups, or an abasic site and the addition of one or more nucleic acid bases to form an "overhang". The modified end prevents or reduces target independent spurious signal development and is later corrected in a target dependent manner to enable amplification.

Oftentimes, the feasibility of a nucleic acid based diagnostic assay is dependent on the ability to amplify the signal generated by only a few molecules of target. Although signal amplification is one potential solution, target amplification is often the preferred solution in nucleic acid based assays. Target amplification involves the repeated copying or duplication of sections of the nucleic acid designated as the target sequence.

One mechanism for target amplification is known as ligase chain reaction (LCR™). In LCR™, two primary probes (first and second, both of same sense) and two secondary probes (third and fourth, both of opposite sense with respect to primary probes) are employed in excess. The first probe hybridizes to a first segment of the target strand and the second probe hybridizes to a second segment of the target strand, the first and second segments being contiguous so that the 3' hydroxyl end of an "upstream" probe abuts the 5' phosphate end of a "downstream" probe, and so that a ligase can covalently ligate the two probes into a fused ligation product.

In like manner, LCR™ employs upstream and downstream secondary probes. A third probe (downstream secondary) can hybridize to the first probe (upstream primary) and a fourth probe (upstream secondary) can hybridize to the second probe (downstream primary) in a similar abutting fashion. Of course, if the target is initially double stranded, the secondary probes can also hybridize to the target complement in the first instance. Once the fused strand of primary probes is separated from the target strand, it will hybridize with the third and fourth (secondary) probes which can be ligated to form a complementary, secondary fused product. In order to understand LCR™ and the improvements described herein, it is important to realize that the fused products are functionally equivalent to either the target or its complement. By repeated cycles of hybridization and ligation, amplification of the target sequence is achieved. This technique is described more completely in EP-A-320 308, the entire disclosure of which is incorporated herein by reference.

One of the great strengths of amplification reactions is their ability to detect exceedingly small numbers of target molecules. However, it is important that the amplification process be highly specific since the amplification of non-target sequences along with signal could potentially impair the reliability of the amplification process. One potential problem associated with ligase chain reaction is background signal caused by target independent ligation of the probes. Since the third probe hybridizes to the first probe and the fourth probe hybridizes to the second probe, the probes, which are added in excess, can easily form duplexes among themselves. These duplexes can become ligated independently of the presence of target to form a fused product which is then indistinguishable from the desired amplified target, yet which is still capable of supporting further amplification. Although target independent ligation of these duplexes is a relatively rare event, it is sufficiently common to cause undesirably high background signals in highly amplified diagnostic assays.

EP-A-439 182 (corresponding to parent application Ser. No. 07/634,77 1 ) describes several mechanisms by which this background or spurious signal in LCR™ can be reduced. One such mechanism involves 3' blocking groups or abasic sites that are "corrected" in the presence of target to yield ends that are ligation competent, i.e. ends that possess the 3' hydroxyl substrate necessary for ligation. The present invention expands and develops these mechanisms, particularly with regard to the use of endonuclease IV as the correction enzyme.

Levin, et al, "Metalloenzymes in DNA Repair", *J. Biol. Chem.* 266(34):22893–22898 (1991) have demonstrated that Endonuclease IV in native form contains zinc, and that inactive enzyme (purified in a metal free buffer) can be reactivated by the addition of certain divalent cations. In particular, $Co^{2+}$ and $Mn^{2+}$ at 200 µM were effective to reactivate the enzymes, depending on the method (EDTA or 1,10-phenanthroline) of inactivation. Johnson and Demple, *J. Biol. Chem.* 263(34):18009–18016 (1988) have shown that the activity of a related enzyme, yeast 3' phosphoglycoaldehyde diesterase, is enhanced by concentrations of $Co^{2+}$ from 3 µM to about 3 mM, above which the cation was inhibitory.

A second potential problem associated with nucleic acid amplification systems is the potential for airborne and carryover contamination. Due to the exponential increase in target sequences, there is an increased potential for some of these molecules to contaminate an untested sample, and to render it falsely positive. Several methods have been described for reducing such contamination. They generally involve destroying substantially all the amplified products either immediately after amplification or immediately prior to the next amplification cycle.

One such contamination control method is taught in co-owned, co-pending application Ser. No. 07/863,622, filed Apr. 3, 1992.

Another method is taught by Walder, et al EP-A-496 483. This document describes the incorporation of ribonucleotides into PCR primers followed by destruction of the amplification products with RNase or alkaline hydrolysis.

While the authors allege that their method is useful in transcription based amplification and in the ligase chain reaction, they have provided no conditions or demonstration of utility except in PCR.

It is well known in the art that DNA ligases will not ligate DNA probes hybridized to a fibonucleotide target. But WO91/17270 describes an LCR variation using fibonucleotide residues at the point of ligation. These residues can later be cleaved by alkali or enzymes to destroy the amplification product and prevent contamination.

However, there is no teaching of using fibo-modified probes in combination with 3' blocking groups as in the present invention. The present invention provides a mechanism for reducing or eliminating contamination in LCR™ using endonuclease IV correction methods. It has been discovered that DNA probes having a single ribonucleotide bearing a 3' blocking phosphate group can be used in LCR™. When so used, the probes alleviate the background caused by target independent ligation and, at the same time, provide a mechanism to control contamination.

SUMMARY OF THE INVENTION

In a first aspect (the "basic modified" method), the invention relates to a method for amplifying a target nucleic acid sequence using LCR, said method including: (a) providing an excess of at least two sets of two probes, the 3' end of an upstream probe being ligated to the 5' end of a downstream probe in the presence of target to form a primary ligation product and the second set of probes hybridizing to the primary ligation product and being ligated to each other to form a secondary ligation product; (b) repeatedly denaturing the hybridized strands, reannealing additional probes and ligating them; and (c) detecting to what extent ligation products have formed, wherein the improvement comprises:

(a) providing in at least one of the upstream probes a 3' end modification such that the probe is incapable of ligation to its downstream partner, said 3' end modification being correctable substantially only when the modified probe is hybridized to the target sequence;

(b) hybridizing the modified probe to the target, if present, to form a modified probe-template complex;

(c) correcting the modification in a target dependent manner using endonuclease IV activity to create a 3' hydroxyl end, thus allowing the corrected probe to be ligated to its downstream partner;

(d) ligating the corrected probe to its downstream partner to form an amplification product; and (e) dissociating the amplification product from the target and repeating the hybridization, correction and ligating steps to amplify the desired target sequence.

Preferably, the 3' modification comprises a blocking moiety (the "blocking" method) such as a blocking moiety of the form:

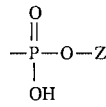

wherein Z is selected from the group consisting of —H; —(CH$_2$)$_n$ CHO, where n is from 1 to about 3; -deoxyribose; and-dideoxyribose. A simple phosphate (Z=H) will do.

The correcting solution preferably includes available divalent cobalt or manganese ion at a concentration of at least about 0.05 mM. The upper range may be 10mM or more, but more preferred ranges include from 0.05 mM to about 2.0 mM, and from about 0.5 mM to about 1.0 mM.

In a variation of the blocking method, the above modified LCR method includes two sets of two probes which are oligodeoxyfibonucleotide probes, except that at least one of said probes includes at least one ribonucleotide residue, preferably the terminal residue containing the 3' modification. Similar blocking modifications may be used, including phosphate at the 3' position of the terminal ribonucleotide residue. Consequently, the blocking method may further comprise, after the detection step, a step of cleaving ligation products using RNase or alkali. In addition or in the alternative, this aspect of the method may further comprise, prior to amplification, a step of cleaving ligation products using RNase.

In yet another aspect (the "abasic" method), the blocking moiety may be a nucleic acid overhang containing an abasic residue immediately 3' to the point of intended ligation. In this case, correction of the modification comprises cleavage of said modified probe on the 5' side of said abasic site, substantially only when said modified probe is hybridized to target or to ligation product.

The correcting solution again preferably includes available divalent cobalt or manganese ion at a concentration of at least about 0.05 mM. The upper range may be 10 mM or more, but more preferred ranges include from 0.05 mM to about 2.0 mM, and from about 0.5 mM to about 1.0 mM.

In a variation of the abasic method two sets of two probes are oligodeoxyribonucleotide probes, except that at least one of said probes includes at least one ribonucleotide residue, preferably immediately 5' to the abasic site. Consequently, the abasic method may further comprise, after the detection step, a step of cleaving ligation products using RNase or alkali. In addition or in the alternative, this aspect of the method may further comprise, prior to amplification, a step of cleaving ligation products using RNase.

In any of the above described methods, detection may be by means of a first hapten (or other specific binding member) attached to the primary upstream and secondary downstream probes; and by a reporter or second hapten (or other specific binding member) attached to the primary downstream and secondary upstream probes. In both cases, the haptens and reporters should be attached to the probes by means which do not significantly affect the hybridization and/or ligation of the probes. This may be done, for example, by attachment at the "outside ends" of the probes. Alternatively, detection may be by means of a blocking moiety which comprises a detectable label and said detecting is by means of monitoring the release of detectable label from the modified probe.

Another aspect of the invention involves a diagnostic kit comprising in combination the following reagents in one or more suitable containers:

(a) two pairs of probes hybridizable with target wherein at least one of the probes is modified such that, when hybridized, a ligase is substantially incapable of acting on the modified probe as its substrate; the two probes capable of hybridizing to target in positions such that, upon correction of said modified probe, the two probes can be ligated to one another (b) a first enzyme reagent having ligase activity for assembling an amplification product; and (c) a second enzyme reagent having endonuclease IV activity capable of correcting the modified probe in a target dependent manner to allow the probe-template complex to be acted upon by the ligase reagent.

The kit may also include any or all of: a) a buffer or means for preparing a buffer containing from 0.05 mM to about 2.0 mM of divalent cobalt ion; and b) an RNase reagent or an alkaline reagent.

A final aspect of the invention is a nucleic acid probe substantially free of naturally occurring nucleic acid fragments, said probe having at least three deoxyribonucleotides covalently linked by phosphodiester linkages to define a 5' and a 3' end of the probe, the probe further comprising a ribonucleotide at the 3' end, the 3' position of the ribonucleotide having attached thereto a group of the formula:

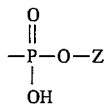

wherein Z is selected from the group consisting of —H; —$(CH_2)_n$ CHO, where n is from 1 to about 3; -deoxyribose; and -dideoxyribose.

Preferably, Z is hydrogen and the oligonucleotide comprises from about 12 to about 50 deoxyribonucleotides.

DETAILED DESCRIPTION

Figure 1:
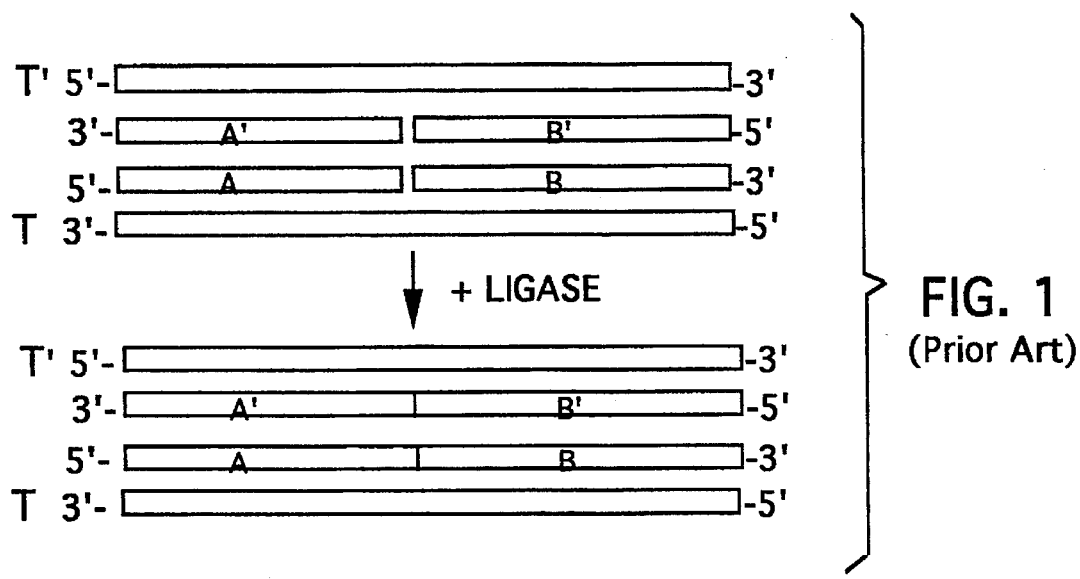
FIG. 1 is a graphic representation of the prior art blunt-ended LCR™. Primary probes A and B hybridize to target and become ligated. Secondary probes A' and B' hybridize to target complement or to fused primary probe product and similarly become ligated.

For purposes of this invention, the target sequence is described to be single stranded. However, this should be understood to include the case where the target is actually double stranded but is simply separated from its complement prior to hybridization with the probes/primers. In the case of double stranded target, secondary, third and fourth probes will also participate in the initial step by hybridizing to the target complement. In the case of single stranded target, the secondary probes will not participate in the initial hybridization step, but will participate in subsequent hybridization steps. Target sequences may comprise deoxyribonucleic acid (DNA) or ribonucleic acid (RNA).

It is to be understood that the term "bases" shall refer to Guanine (G), Cytosine (C), Adenine (A) and Thymine (T) when the context is that of DNA; and Guanine (G), Cytosine (C), Adenine (A) and Uracil (U) in the context of RNA. The term also includes analogs and derivatives of the bases named above, provided they can undergo hydrogen bonding of base pairs characteristic of the natural bases. Exemplary base "analogs" can be found in 1114 Official Gazette, at 43. Although the degenerate base Inosine (I) may be employed with probes used in this invention, it is not preferred to use I within modified portions of the probes according to the invention. Individual nucleotides or bases are said to be "complementary" if they result in canonical base pairing; e.g. C with G, and A with T or U.

Throughout this application, the "prime" (') designation is used to indicate a complementary base or sequence. One oligonucleotide is "complementary" to another if it hybridizes to the other and has substantially complementary base pairings in the hybridized region. Thus, probe A can be complementary to A' even though it may have ends not coterminal with A'. The same is true of B and B'. As a result of this definition, "complementary" oligonucleotide sequences encompass sequences that have mismatched base pairs in the hybridizable region, provided they can be made to hybridize under assay conditions.

It is an important feature of the present invention that, instead of using complementary pairs of probes capable of forming ligatable, blunt-ended duplexes, at least one probe of one of the probe pairs initially includes a "modified" end which renders the resultant primary or secondary probe not a suitable substrate for the ligase catalyzed fusion. A "modified end" is defined with respect to the point of ligation rather than with respect to its complementary probe. A "modified end" has either (1) a blocking moiety (or additional base residues) on a group (e.g. the 5' phosphate or the 3' hydroxyl) which, under ordinary LCR™ conditions, obligatorily participates in the ligase catalyzed fusion (See e.g. probe A of FIG. 2); or (2) omitted bases to create a "gap" between one probe terminus and the next probe terminus.

By convention in this application, a modified end of the first type is referred to as an "overhang", the overhang being an additional blocking moiety or additional base residues which, when hybridized to the target sequence extends beyond the point of ligation. The term "overhang" is not to be confused with an "extension" of one probe with respect to its complementary probe, resulting from the fact that they need not be coterminal. A modified end of the second type is referred to herein as a "recess", the recess being the gap between two primary or secondary probes after hybridizing to the target. The presence of these modified ends reduces the falsely positive signal created by target independent ligation of complementary probe duplexes to one another in the absence of target.

"Correction" of the modification is subsequently carried out to render the probes ligatable. As used herein "correction" refers to the process of rendering, in a target dependent manner, the two primary probes or the two secondary probes, or both, ligatable to their same sense partners. Thus, only those probes hybridized to target, target complement or polynucleotide sequences generated therefrom are capable of being "corrected". "Correction" can be accomplished by several procedures, depending on the type of modified end used, although endonuclease IV corrections are examined herein.

As used herein, "point of ligation" or "intended point of ligation" refers to a specific location between two probe partners that are to be ligated in a template-dependent manner. It is the site at which the "corrected" upstream probe lies adjacent its downstream partner in 5' phosphate-3' hydroxyl relationship. For each set of four LCR™ probes there are two "points of ligation", a point for the primary probe partners and a point for the secondary probe partners.

In conventional LCR™, typically the two points of ligation are opposite one another, thus forming blunt ended duplexes when the probe pairs hybridize to one another. In the present invention, the points of ligation may be opposite one another or displaced from one another (preferably with 3' extensions) by one or more bases. The exact point(s) of ligation varies depending on the embodiment and, thus, this term is further defined in the context of each embodiment.

Each of the probes may comprise deoxyribonucleic acid (DNA) or ribonucleic acid (RNA). It is a routine matter to synthesize the desired probes using conventional nucleotide phosphoramidite chemistry and the instruments available from Applied Biosystems, Inc, (Foster City, Calif.); DuPont, (Wilmington, Del.); or Milligen, (Bedford, Mass.). Phosphorylation of the 5' ends of the probes, a necessity for ligation by ligase, may be accomplished enzymatically by a kinase, as is known in the art, or by any chemical synthetic method known to phosphorylate 5' ends. Commercial reagents are available for this purpose for use with automated synthesis. As will be seen, similar methods and reagents are used to place a blocking phosphate on a 3' probe end.

In general, the methods of the invention comprise repeated steps of (a) hybridizing the modified probes to the target (and, if double stranded so that target complement is present, to the target complement); (b) correcting the modification in a target dependent manner to render the probes ligatable; (c) ligating the corrected probe to its partner to form a fused or ligated product; and (d) dissociating the fused product from the target and repeating the hybridization, correction and ligation steps to amplify the desired target sequence. Steps (a), (c) and (d) are essentially the same for all of the embodiments and can be discussed together. They are generally the same steps that one would employ in conventional LCR™. Step (b) varies depending on the type of modification employed and. correction by endonuclease IV is discussed herein.

Hybridization of modified probes to target (and optionally to target complement) is adequately explained in the prior art; e.g EP-320 308 and EP 439 182. Probe length, probe concentration, GC content and stringency of conditions all affect the degree and rate at which hybridization will occur. Preferably, the probes are sufficiently long to provide the desired specificity; i.e, to avoid being hybridizable to random sequences in the sample. Typically, probes on the order of 15 to 100 bases serve this purpose. Presently preferred are probes having a length of from about 15 to about 40 bases.

The probes are generally added in approximately equimolar concentration since they are expected to react stoichiometrically. Each probe is present in a concentration ranging from about 5 nanomolar (nM) to about 90 nM; preferably from about 10 nM to about 85 nM. The optimum quantity of probe used for each reaction also varies depending on the number of cycles which must be performed. Optimum concentrations can readily be determined by one of ordinary skill in this art The stringency of conditions is generally known to those in the art to be dependent on temperature, solvent and other parameters. Perhaps the most easily controlled of these parameters is temperature and thus it is generally the stringency parameter varied in the performance of LCR™. Since the stringency conditions required for practicing this invention are not unlike those of ordinary LCR™, further detail is deemed unnecessary, the routine practitioner being guided by the examples which follow.

The next step in the general method follows the specific correction step and comprises the ligation of one probe to its adjacent partner. Thus, primary upstream probes are ligated to their associated primary downstream probes and secondary upstream probes are ligated to their associated secondary downstream probes. An "adjacent" probe is either one of two probes hybridizable with the target in a contiguous orientation, one of which lies with its phosphorylated 5' end in abutment with the 3' hydroxyl end of the partner probe. "Adjacent" probes are created upon correction of the modified end(s) in a target dependent manner. Since enzymatic ligation is the preferred method of covalently attaching two adjacent probes, the term "ligation" will be used throughout the application. However, "ligation" is a general term and is to be understood to include any method of covalently attaching two probes.

The conditions and reagents which make possible the preferred enzymatic ligation step are generally known to those of ordinary skill in the art and are disclosed in the references mentioned in background. Ligating reagents useful in the present invention include prokaryotic ligases such as *E coli* ligase, T4 ligase and *Thermus thermophilus* ligase (e.g., ATCC 27634) as taught in EP-320 308 and EP-A-373 962. This latter ligase is presently preferred for its ability to maintain activity during the thermal cycling of LCR™. Suitable thermally stable ligases are commercially available from New England Biolabs, Inc. (Beverly, Mass.), Epicentre Technologies, Inc. (Madison, Wisc.) and Molecular Biology Resources (Milwaukee, Wisc.). Absent a thermally stable ligase, the ligase must be added again each time the cycle is repeated. Also of potential utility are eukaryotic ligases, e.g. DNA ligase of Drosophilia, reported by Rabin, et al., *J. Biol. Chem.* 261: 10637– 10647 (1986).

Once ligated, the fused probe is dissociated (e.g. melted) from the target and, as with conventional LCR™, the process is repeated for several cycles. The number of repeat cycles may vary from 1 to about 100, although from about 15 to about 70 are preferred presently.

It is desirable to design probes so that when hybridized to their complementary (secondary) probes, the ends away from the point of intended ligation (i.e. "outside" ends) are not free themselves to participate in other unwanted ligation reactions. Thus, ligatable sticky or blunt outside ends should be avoided. Free 5' terminal phosphates should be avoided or eliminated, especially if such sticky or blunt ends must be used. This can be accomplished either through synthesizing oligonucleotide probes (which normally carry no 5' terminal phosphate groups), or through the use of phosphatase enzymes to remove terminal phosphates (e.g. from oligonucleotides generated through restriction digests of DNA). Alternatively, ligation of the outside ends of the probes can be prevented by blocking the end of at least one of the probes with a "hook" or other reporter molecule or marker moiety as will be described in detail below.

It is also desirable to design the probes so that substantially all of the amplification products made can be selectively inactivated or destroyed to reduce the risk of contamination. To be effective, such inactivation must destroy substantially all the amplification products and it may occur at various times during the process. Generally inactivation may occur immediately after amplification, after detection or immediately prior to the next LCR™ reaction. For convenience these will be referred to herein as "postamplification", "post-detection" and "pre-amplification", respectively. An inactivation method that is used pre-amplification must selectively destroy amplification product without destroying the reactant probes and reagents. An inactivation method that is used post-detection does not share this constraint.

For example, a ribonucleotide residue can be incorporated into an otherwise deoxyribo-oligonucleotide and the resultant product can be cleaved by RNase or alkaline hydrolysis conditions. Particularly useful among the RNases reported in the literature are RNaseH, which cleave ribonucleotides in RNA:DNA duplexes and in single stranded RNA. Although *E coli*. Rnase generally prefers a string of about 4 ribonucleotides for efficient cutting, Walder, et al. have reported a human RNase H activity in K562 erythroleukemia cells, designated RNaseHI (see EP-A-496 483), which is said to cleave mixed R/DNA:DNA duplexes when only a single ribo residue is present. The procedure by which this is accomplished is described in greater detail in EP-A-496 483 and in WO91/17270.

It is also possible to cleave the ribo-modified products using alkaline conditions. In the context of this application, "alkaline conditions" refers to conditions above a pH of 7.0 which are sufficient to effect a hydrolysis of the phosphodiester bond adjacent a ribonucleotide moiety. Usually a pH above about 10 for 0.5 to 2 hours with heat will produce hydrolysis. Typical conditions are known in the art and include by way of example, not limitation, treatment with 0.6N NaOH for 30 min to 1 h at 90° C. or with 30–40 mM KOH or NaOH for 1–1.5 hours. A 36 mM solution of KOH produces a pH of about 11. Other probe modifications that permit destruction after ligation are also within this invention.

MODIFIED ENDS CORRECTABLE BY ENDONUCLEASE IV

As mentioned, a first embodiment involves a modified end wherein a blocking moiety or additional bases are added to the 3' end of at least one upstream probe, beyond the point of intended ligation. The blocking moiety or the additional bases comprise the "overhang" and are the reason blunt-end ligation is not possible.

Modified Probe Reagents. In a first variation depicted schematically in FIG. 2 and exemplified in Examples 5–7, the overhang comprises a chemical blocking agent, R. It is well known that the standard DNA ligase reaction requires that the substrate strands present a 3' hydroxyl and a 5' phosphate at the point of ligation. Several modifications, particularly at the 3' hydroxyl group, are known to introduce an R group which will render the modified end incapable of participating in a ligase reaction, but which can be removed when the modified strand is part of a double stranded structure. Such modifications include the following illustrative R groups attached to the 3' oxygen in place of the hydrogen atom:

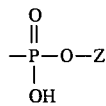

wherein Z is selected from the group consisting of —H; —(CH$_2$)$_n$ CHO, where n is from 1 to about 3, preferably 1 or 2;-deoxyribose; and -dideoxyribose.

The synthesis of probes having ends suitably modified with an R group is well known in the art. For example, chemical synthesis of oligonucleotides containing a 3' phosphate group has been described by Markiewicz and Wyrzykiewicz, Nucl. Acids Res. 17:7149–7158 (1989). Larger blocking groups, which may have the advantage of hiding the 3' phosphate from non-specific phosphatases that might be present in some samples, are conveniently prepared by creating the oligonucleotide probe with terminal transferase and dUTP or ddUTP, followed by treatment with uracil glycosylase. Purification of uracil glycosylase is taught by Lindahl, et al, J.B.C. 252:3286–3924 (1977). In the case of dUTP addition, treatment with strong alkali following the uracil glycosylase treatment can be used to prepare the glycoaldehyde derivative. It is to be understood that the examples of R groups given above are illustrative only, and that one of ordinary skill could synthesize many variants which would work equally well. In addition, example 16 describes a convenient automated synthesis of a probe having a 3' terminal phosphate.

In another variation, the probes are modified to contain both a 3' ribonucleotide moiety and a 3' phosphate blocking moiety. Synthesis of such probes is described in Examples 14–17. These probes have dual advantages. They avoid the problem of target independent ligation by virtue of the 3' blocking phosphate. In addition, they avoid the problems of contamination because the amplification products can be cleaved and destroyed at the ribonucleotide residue by various RNases or alkaline conditions.

Any contamination control method that cleaves the amplification product may be used post-detection. Either RNase or alkaline conditions can be used to cleave the ligation product at the ribonucleotide when the reaction is completed. However, for preamplification contamination control, RNase is preferred. While alkaline conditions will cleave ligation products to leave a 5' hydroxyl, it also demonstrates a tendency to act on unligated ribo-modified probe reagents to convert 3' phosphates to 2' phosphates. It is not known whether or how efficiently the 2' phosphated probes can be ligated. In contrast, preferred RNases cut the ligation products leaving a 5' hydroxyl and a 3' phosphate. In other words, RNase cleaves a phosphodiester bond on the 3' or downstream side of the ribo residue, a bond that does not even exist in the unligated modified reagents. Thus, RNase can be used as a pre-amplification contamination control without damaging the amplification reagents which still need to perform.

The RNase may be, and preferrably is, thermolabile since it should not retain activity after LCR™ begins.

Figure 3:
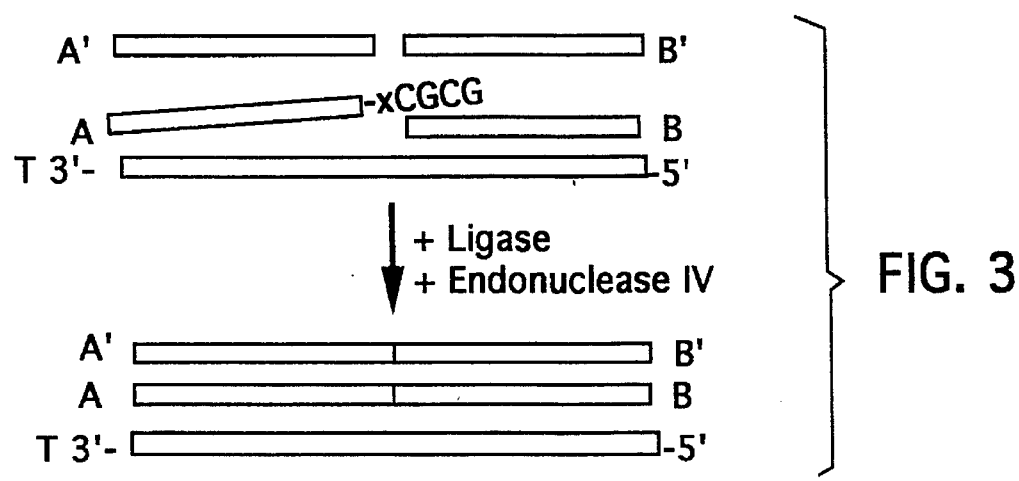
FIG. 3 is another graphic representation of the improved LCR™ according to the invention. In this case, abasic site modified upstream probe A cannot be ligated directly to its downstream partner B; but after correction (cleavage at the abasic site "x" by Endonuclease IV when probe A is hybridized to target) a 3' hydroxyl is restored and ligation to B is possible.

In yet another variation of overhanging ends, the overhang consists of additional nucleic acid bases which can be cleaved off once the probes are hybridized to target. This variation is depicted schematically in FIG. 3 and exemplified in Examples 3-4 and 8-9. The overhang prevents ligation at the intended point of ligation by virtue of its bulk, and stereochemically blocks or masks the group(s) which obligatorily participate in the ligase reaction (as described above for blocked ends). What distinguishes this from the simple chemical blockage described above is the nature and size of the "blocking" group (i.e., the overhang). It is by nature composed of nucleic acid residues colinear with the probe molecule. However, the size of the group is too large to permit the modified end of the molecule to remain in the vicinity of the ligation point when hybridized to a target.

Although several classes of overhangs are possible, (three are described in the parent applications) the phosphate-blocked and abasic site overhangs are further considered herein. In general, the overhang should be complementary to the target so that its removal can be template dependent as is described below. The overhang may be from 1–10 bases, preferably from 1–5 bases in length. The synthesis of oligonucleotides with abasic sites has been described in the literature. See, for example, Takeshita, et al, *J. Biol. Chem.* 262:10171–10179 (1987); and Eritja, et al. Nucleosides & Nucleotides 6(4):803–814 (1987). Modified oligonucleotide probes can be synthesized so as to position an abasic site immediately 3' to the point of ligation on the probe intended to donate its 3' end.

Figure 2:
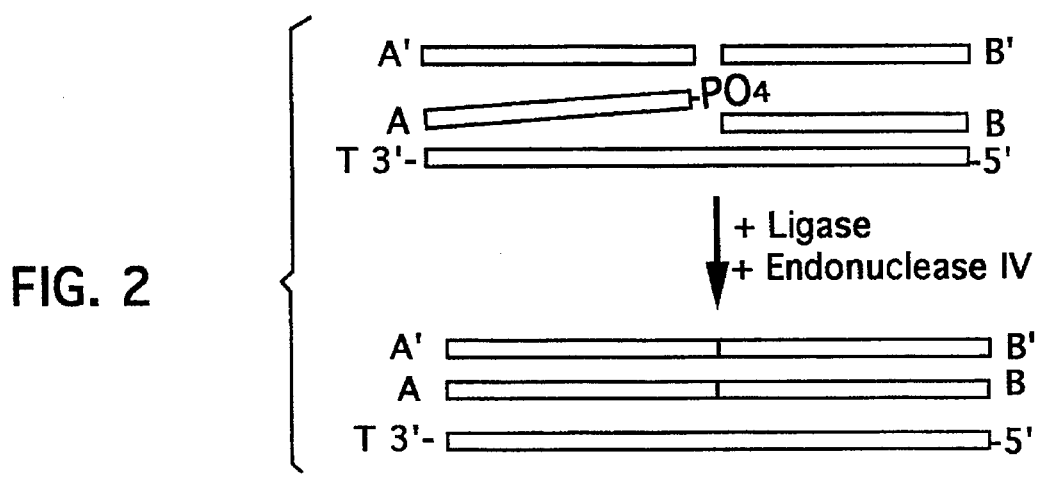
FIG. 2 is graphic representation of the improved LCR™ according to the invention. Upstream probe A is modified to include blocking phosphate groups on its 3' end where a 3' hydroxyl is needed for ligation. Correction (phosphate removal by Endonuclease IV when probe A is hybridized to target) leaves a 3' hydroxyl and ligation to downstream probe B is possible.

For both blocked and abasic modified probes, the probes are preferably designed to minimize correction that might take place while the probe is hybridized to its complementary probe (as opposed to correction while hybridized to true target). With reference to FIG. 2 for example, when the 5' terminus of A' is coterminal with the 3' phosphate blocked probe A there may be some tendency for endonuclease IV to recognize this as its double stranded substrate and to cleave a 3' phosphate from A even in the absence of target. Similarly, in FIG. 3, when the 5' terminal base of A' is opposite the abasic site, x, of probe A, and even when opposite the residue immediately 5' of the abasic residue in probe A, there may be some tendency for endonuclease IV to recognize this as its double stranded substrate and to cleave the overhang from A at the abasic site even in the absence of target. Both of these adverse situations can be minimized by staggering or offsetting the ends of modified probes A (and/or B') so that they extend as single strands beyond the ends of their complementary probes. Furthermore, in the case of the abasic modification, the abasic site itself preferably lies beyond the 5' end of the complementary probe by at least one or more bases. In other words, the 5' terminal residue of the complementary probe A' lies opposite a nucleotide residue in the upstream probe A which is at least one residue 5' to the site of the modification.

In the phosphate blocked situation, this is illustrated by example 7, using probe AA123-1P(20) complementary to AA123-3(18), and probe AA123-4P(22) complementary to AA123-2 (a 20-mer). Similarly, in the abasic site situation, this is demonstrated by example 8 using probes AA 123-1E 1 complementary to AA 123-3( 18), and probe AA123-4E1 complementary to AA123-2 (a 20-mer). In each of these cases, the 3' modification extends beyond the 5' end of the complementary probe, virtually assuring that endonuclease IV will not mistake this duplex for its true substrate, modified probe on complete target strands.

Enzymology. The enzyme endonuclease IV (Siwek, et al, Nucl. Acids Res. 16:5031–5038 (1988) sometimes referred to herein as "Endo IV") and a variety of other naturally occurring enzymes are capable of removing various blocking groups to expose a 3' hydroxyl group if and substantially only if the strand containing the blocking group is hybridized to a complementary strand. For example, Doetsch and Cunningham, *Mutation Research*, 236:173–201 (1990) describe in detail the enzymology of endonucleases and the chemistry of several different reactive abasic sites. The same enzyme has also been shown to cleave a polynucleotide at an abasic site if the polynucleotide is hybridized to a complementary strand. Endonuclease IV is a class II AP endonuclease, which effects cutting on the 5' side of the abasic site, leaving a 3' hydroxyl end on the polynucleotide. By both its position and its chemical nature, the polynucleotide is now capable of being joined by ligase to an adjacent probe.

While use of the endonuclease IV referred to herein is clearly within the scope of the invention, it will be recognized that many other equivalent correcting reagents may be employed. For example, other enzymes may be discovered that have a similar ability to correct the modifications substantially only when the modified probe is hybridized to target. Also, it may be found that the entire enzyme is not essential, but that some fragment or digest of the enzyme will have the desired activity. Finally, it may be that desired activity may be obtained by recombinantly produced polypeptides having only a fraction of the length of the native protein. All such variations are deemed equivalents of Endonuclease IV for purposes of this invention.

If the endonuclease IV enzyme is not thermostable, it should be re-added at each cycle of LCR™. However, it is preferred to use endonuclease isolated or recombinantly engineered from a thermos table species, such as the *T. thermophilus* Endo IV described in copending and co-owned U.S. applications Ser. Nos. 07/860,861 and 07/869,306, filed on Mar. 31, 1992 and Apr. 16, 1992, respectively, the entire disclosures of which have been incorporated herein by reference. *E. coli* strain CS1 carries plasmid pTT7 containing an insert coding for this enzyme was deposited with the American Type Culture Collection (ATCC) at 12301 Parklawn Drive, Rockville, Md. on Apr. 9, 1992 and has been given Accession No.68950. In the context of the present application, "thermostable" means that the enzyme reagent retains a substantial portion of its activity at temperatures in excess of about 70° C.; preferably in excess of about 80° C.

It has been shown by Levin, et at, "Metalloenzymes in DNA Repair", *J. Biol. Chem.* 266(34):22893–22898 (1991) that Endonuclease IV in native form contains Zinc. These researchers have also shown that endonuclease IV which has been purified in a metal free buffer is inactive, but it can be reactivated by the addition of certain divalent cations. In particular, $Co^{2+}$ and $Mn^{2+}$ at 200 µM were effective to reactivate the enzymes, depending on the method (EDTA or 1,10-phenanthroline) of inactivation. Others have shown that the activity of a related enzyme, yeast 3' phosphoglycoaldehyde diesterase, is enhanced by concentrations of $Co^{2+}$ from 3 gM to about 3 mM, above which the cation was inhibitory.

However, it has surprisingly been found that $Co^{30}$ is inhibitory to the performance of ligase and LCR™ generally. For example, see Examples 12 and 13, infra, wherein concentrations above about 2 mM prevented all amplification from $10^6$ targets. Thus, it was necessary to find the window of concentration of $Co^{2+}$ which enabled the endonuclease IV without inactivating the LCR™ (apparently the ligase itself). Since $Co^{2+}$ is very tightly bound by chelators such as EDTA, and it is difficult to completely remove EDTA often used in the preparation of samples, it is useful to refer to "available" cobalt ion, which is the amount in excess of that bound by any chelator present. If careful measures are taken to avoid introducing or to completely remove chelator, then the "available" cobalt ion concentration approximates the actual concentration. It is believed that the available concentration of $Co^{2+}$ should be about 0.05 to about 2.0 mM, usually about 0.1 to about 1.5 mM, preferably about 0.5 to about 1 mM. Cobalt ion is suitably supplied as any common salt, such as the dichloride salt.

Applicants have also discovered surprisingly that the divalent cation $Mn^{2+}$ will substitute for $Co^{2+}$ but not for $Mg^{2+}$ in the LCR™ involving endonuclease IV. This is surprising because literature reports establish that $Mn^{2+}$, as the sole divalent cation, will support ligase activity and endonuclease IV activity. However, $Mn^{2+}$ alone is not sufficient to support the LCR or endo IV modified LCR. The presence of $Mg^{2+}$ is still a requirement for the amplification reactions. Preferably the $Mg^{2+}$ concentration is at least about 0.5 mM, and ideally is from about 5 to about 20 mM.

Detection. Following amplification, the amplified sequences can be detected by monitoring the formation of ligated product using a number of conventional technologies known in the art. In one preferred way, formation of the ligated product is monitored using the fact that a new covalent bond is formed between the first and second probes of the same sense. Thus, amplification product is longer than the individual probes and can be separated form unligated probes on this basis. Separation may easily be achieved by gels or by affinity members or "hooks". A "hook" is any moiety having a specific ligand-receptor affinity. It may be, for example, a hapten or a segment of polynucleotide. A hook may be attached to one probe and a label may be attached to the other probe of same sense. Ligation joins the label to the affinity moiety and separated label can be measured on a solid phase following separation.

Alternatively, hooks may be provided at the available outside ends of at least two probes (opposite ends of fused product), and preferably to the outside ends of all four probes. Typically, the hook(s) at one end of the fused product (e.g. the 5' end of A and the 3' end of A') comprises a first hapten capable of being immobilized by a reagent (such as antibody or avidin) coated onto a solid phase. The hook(s) at the other end (e.g. the 3' end of B and the 5' end of B') contains a different antigen or hapten capable of being recognized by a label or a label system such as an antibody-enzyme conjugate. In the case of an enzyme conjugate, a substrate is then added which is convened by the enzyme to a detectable product.

Exemplary hapten hooks include many drugs (e.g. digoxin, theophylline, phencyclidine (PCP), salicylate, etc.), T3, biotin, fluorescein (FITC), dansyl, 2,4-dinitrophenol (DNP); and modified nucleotides such as bromouracil and bases modified by incorporation of a N-acetyl-7-iodo-2-fluorenylamino (AIF) group; as well as many others. Certain haptens are disclosed in co-pending, co-owned patent applications U.S. Pat. No. 7/808,508 (adamantaneacetic acids), U.S. Pat. No. 07/808,839 (carbazoles and dibenzofurans), both filed Dec. 17, 1991, U.S. Pat. No. 07/858,929 (acridines), and U.S. Pat. No. 07/858,820 (quinolines), both filed Mar. 27, 1992 (collectively referred to herein as the "hapten applications"). The entire disclosure of each of the above hapten applications is incorporated herein by reference.

Virtually any hapten can be used with the present invention. The invention requires only that a specific binding partner is known or can be prepared (a definitional property of "hapten") and that the hapten can be coupled to the probe such that it does not interfere with hybridization or ligation. Many methods of adding haptens to probes are known in the literature. Enzo Biochemical (New York) and Clontech (Palo Alto) both have described and commercialized probe labelling techniques. For example, a primary amine can be attached to a 3' oligo end using 3'-Amine-ON CPG$^m$ (Clontech, Palo Alto, CA). Similarly, a primary amine can be attached to a 5' oligo end using Aminomodifier II® (Clontech). The amines can be reacted to various haptens using conventional activation and linking chemistries.

Publications WO92/10505, published 25 June 1992 and WO 92/11388 published 9 July 1992 teach methods for labelling probes at their 5' and 3' ends respectively. According to one known method for labeling an oligonucleotide, a label-phosphoramidite reagent is prepared and used to add the label to the oligonucleotide during its synthesis. For example, see Thuong, N. T. et al., *Tet. Letters*, 29(46):5905–5908 (1988); or Cohen, J. S. et al., U.S. patent application 07/246,688 (NTIS ORDER No. PAT-APPL-7-246,688) (1989).

In another embodiment of this invention, detection is achieved not by directly measuring formation of the ligated product, but by measuring release of the blocking moiety or the overhang. This can easily be done if the blocking moiety or overhang contains a detectable label. In this case, a reduction in signal associated with the solid phase indicates the presence of target. In a preferred variation the label is a fluorophore having a first characteristic spin property when attached to the probe, and a second, distinguishable spin property when released from the probe. Such labels are well known in the an of fluorescence polarization assays. See, for example, EP-A-382 433 (ICI). Coupling these labels to blocking moiety or to a nucleic acid overhang is a matter of routine chemistry.

EXAMPLES

The invention will now be described further by way of examples. The examples are illustrative of the invention and are not intended to limit it in any way.

Examples 1–2 below, illustrate enhanced LCR™ using probes having modified ends which are corrected by endonuclease IV. Both blocking phosphate groups and abasic site overhangs are demonstrated. The probe sequences are given in Tables I–IV below. The probes are specific for a target DNA sequence at position 123 or 250 in *Actinobacillus actinomycetemcomitans*, hence the designation "AA123" or "AA250". The next numeral (after the dash) designates the position of the probe in a set of four: Probes numbered −1 and −2 have the same 5'–3' orientation while probes numbered −3 and −4 have the opposite sense. Probes numbered −1 and −3 hybridize, as do probes numbered −2 and −4.

"P" and "p" indicate a phosphate group. This is normal and required on a 5' terminus, but serves as a ligation blocking modification on a 3' end. 3' phosphorylated probes were synthesized by initiating automated synthesis with 2-[[2-[(4,4'-dimethoxytrityl)oxy] ethyl] sulfonyl]ethyl 2-cyano-ethyl N,N-diisopropylphosphoramidire (Horn, T and Urdea, M *Tet. Lett.* 27 4705+ (1986)) as reported (Ashely, GW and Kushland, DM *Biochemistry* 30:2927–2933 (1991)), followed by the sequential addition of ribonucleofide and deoxyribonucleotide cyanoethyl phosphoramidites using an automated DNA synthesizer.

"E" and "x" designate an abasic site (described further below). A number (1, 3 or 5) following the "E" designates the length of complementary bases (overhang) beyond the abasic site. Numbers in parentheses represent probe lengths. Abasic probes were synthesized on automated instruments using modified phosphoramidite reagents according to the method of Eritja, et al. *Nucleosides & Nucleotides* 6(4):803–814 (1987). All probes are oligodeoxyribonucleotides except as specified.

The target DNA used in examples 1–12 and 14–17 was a plasmid containing an 898 base pair insert isolated from *Actinobacillus actinomycetemcomitans*. (ATCC Acc. No. 53219). The plasmid was digested with EcoRI and PstI to liberate an approximately 1000 base pair fragment. Plasmid concentrations were determined spectrophotometrically assuming an O.D. equal to 1.0 corresponds to a DNA concentration equal to 50 µg/mL. Target DNA solutions were made by serially diluting the digested plasmid in 5 mM Tris pH 7.8, 0.1 mM EDTA and 300 µg/mL human placental DNA.

All reactions, unless otherwise stated, were performed in LCR Buffer (45 mM EPPS pH 7.8, 80 mM KCl, 10 mM MgCl$_2$, 10 mM NH$_4$Cl and 0.5 mM NAD$^+$) supplemented with acetylated bovine serum albumin (BSA) and temperature cycling was achieved with a COY Model 50 temperature cycler. Reactions were terminated by transferring aliquots into Stop Buffer (80% formamide, 20 mM EDTA, 0.05% (w:v) xylene cyanol and 0.05% bromophenol blue).

The ligated and unligated products were resolved on a 16×20×0.04 cm 15% polyacrylamide gel containing 8.3 M urea in 80 mM Tris, 80 mM boric acid pH 8.0, 1.0 mM EDTA. The gel was autoradiographed, the autoradiograph used as a template to excise the ligated and unligated probes and the amount of radioactivity in each band was measured by liquid scintillation counting. The percentage of radioactivity in the ligated product was calculated as a function of the total counts in each lane.

Unless otherwise stated, the following abbreviations have the meaning indicated.

| | |
|---|---|
| BSA | bovine serum albumin |
| EDTA | a metal chelator, ethylenediamine tetraacetic acid |
| EPPS | a buffer comprising N-(2-hydroxyethyl)-piperazine-N'-(3-propanesulfonic acid) |
| HPLC | high performance liquid chromatography |
| NAD or NAD+ | nicotine adenine dinucleotide |
| Tris | a buffer comprising tris(hydroxymethyl)aminomethane |
| TTh | *Thermus thermophilus* |

TABLE I

AA PROBE SETS TO Position 123 of
*ACTINOBACILLUS ACTINOMYCETEMCOMITANS*

| Designation | SEQUENCE | SEQ ID No. |
|---|---|---|
| AA123-1 (20) | 5'-TTGTCGAGCACCTTGAATAA -3' | 1 |
| AA123-1P (20) | 5'-TTGTCGAGCACCTTGAATAAp -3' | 2 |
| AA123-1-E1 | 5'-TTGTCGAGCACCTTGAATAAxT -3' | 3 |
| AA123-1-E3 | 5'-TTGTCGAGCACCTTGAATAAxTAA -3' | 4 |
| AA123-1-E5 | 5'-TTGTCGAGCACCTTGAATAAxTAATG -3' | 5 |
| AA123-2 | 5'-      pTTAATGGCTTCGATTGGGCT-3' | 6 |
| AA123-3 (20) | 3'-AACAGCTCGTGGAACTTATTp -5' | 7 |
| AA123-3 (18) | 3'-AACAGCTCGTGGAACTTAp -5' | 8 |
| AA123-4P (22) | 3'-      pTTAATTACCGAAGCTAACCCGA-5' | 9 |
| AA123-4P (20) | 3'-      pAATTACCGAAGCTAACCCGA-5' | 10 |
| AA123-4 (20) | 3'-      AATTACCGAAGCTAACCCGA-5' | 11 |
| AA123-4-E1 | 3'-      TxTTAATTACCGAAGCTAACCCGA-5' | 12 |
| AA123-4-E3 | 3'-      CTTxTTAATTACCGAAGCTAACCCGA-5' | 13 |
| AA123-4-E5 | AACTTxTTAATTACCGAAGCTAACCCGA-5' | 14 | where x = abasic site; p = 3' - phosphate blocking group; and p = 5' - phosphate group (normal ligation substrate)

TABLE II

AA PROBE SETS TO Position 250 of
*ACTINOBACILLUS ACTINOMYCETEMCOMITANS*

| Designation | SEQUENCE | SEQ ID No. |
|---|---|---|
| AA250-1 | 5'-CCGATTGCAATGTAATATCGACGTC 3' | 15 |
| AA250-1E5 | 5'-CCGATTGCAATGTAATATCGACGTCxTCGGC 3' | 16 |
| AA250-2 | 5'      pGTCGGGCAAATAATTCGCCAC-3' | 17 |
| AA250-3 (24) | 3'-GCTAACGTTACATTATAGCTGCAGp -5' | 18 |
| AA250-3 (22) | 3'-GCTAACGTTACATTATAGCTGCp -5' | 19 |
| AA250-4 (19) | 3'-      CAGCCCGTTTATTAAGCGG-5' | 20 |
| AA250-4 (21) | 3'-      AGCAGCCCGTTTATTAAGCGG-5' | 21 | where x = abasic site; p = 3' - phosphate blocking group; and p = 5' - phosphate group. (normal ligation substrate)

TABLE III

Synthetic Target Molecules

For AA123 Probe Sets

AA123TAR-3/4    5'-TTGTCGAGCACCTTGAATAATTAATGGCTTCGATTGGGCT-3'    22

AA123TAR-1/2    3'-AACAGCTCGTGGAACTTATTAATTACCGAAGCTAACCCGA-5'    23

Substrate For Abasic Nuclease Detection

E4SUB1    $C^{AA}C_{GGATCCGGCT\,x\,TTTTTGGGG}$-3'    24
            $A\,C_{ATG}CCTAGGCCGAAAAAAA$-5' where x = abasic site.

EXAMPLE 1: Blunt-End LCR™

LCR™ was performed using the blunt-ended probe set (see Table I) consisting of AA123-1(20), AA123-2, AA123-3(20) and AA123-4(20) in a 20 gL reaction volume containing LCR Buffer supplemented with 10 µg/mL BSA and 300 ng of human placental DNA. Each probe was present at 83 nM (approximately 5% of probe 2 was 3'-end labeled with [$\alpha$-$^{32}$P]-cordycepin triphosphate to enable detection) and the final concentration of *Thermus thermophilus* (Tth) DNA ligase equalled 0.15 µg/mL. Duplicate reactions containing either zero or $10^6$ molecules of target DNA were performed. The samples were overlaid with 15 gL of mineral oil and the temperature cycle consisted of a 90° C. incubation for 30 seconds followed by a 50° C. incubation for 30 seconds. At specified cycles (see Table E-1), 1.4 gL aliquots were removed, mixed with 2.0 µL of stop buffer, heated to 90° C. for 2 min and applied to a denaturing polyacrylamide gel. Table E-1 shows the average percent ligated and the ratio of (+)/(−) target for the duplicate reactions. The data show that $10^6$ targets are distinguishable from zero targets. However, other data show that detection of fewer than $10^5$ were not adequately reproducible using unmodified probes.

TABLE E-1

| | Blunt-End LCR | | |
|---|---|---|---|
| | Percent Ligated | | |
| Cycle No. | 0 Targets | $10^6$ Targets | Ratio (+/−) Target |
| 25 | 1.65 | 32.17 | 19.5 |
| 28 | 5.76 | 41.88 | 7.3 |
| 31 | 14.55 | 52.27 | 3.6 |
| 34 | 23.28 | 59.97 | 2.6 |
| 37 | 34.11 | 65.20 | 1.9 |

Figure 4:
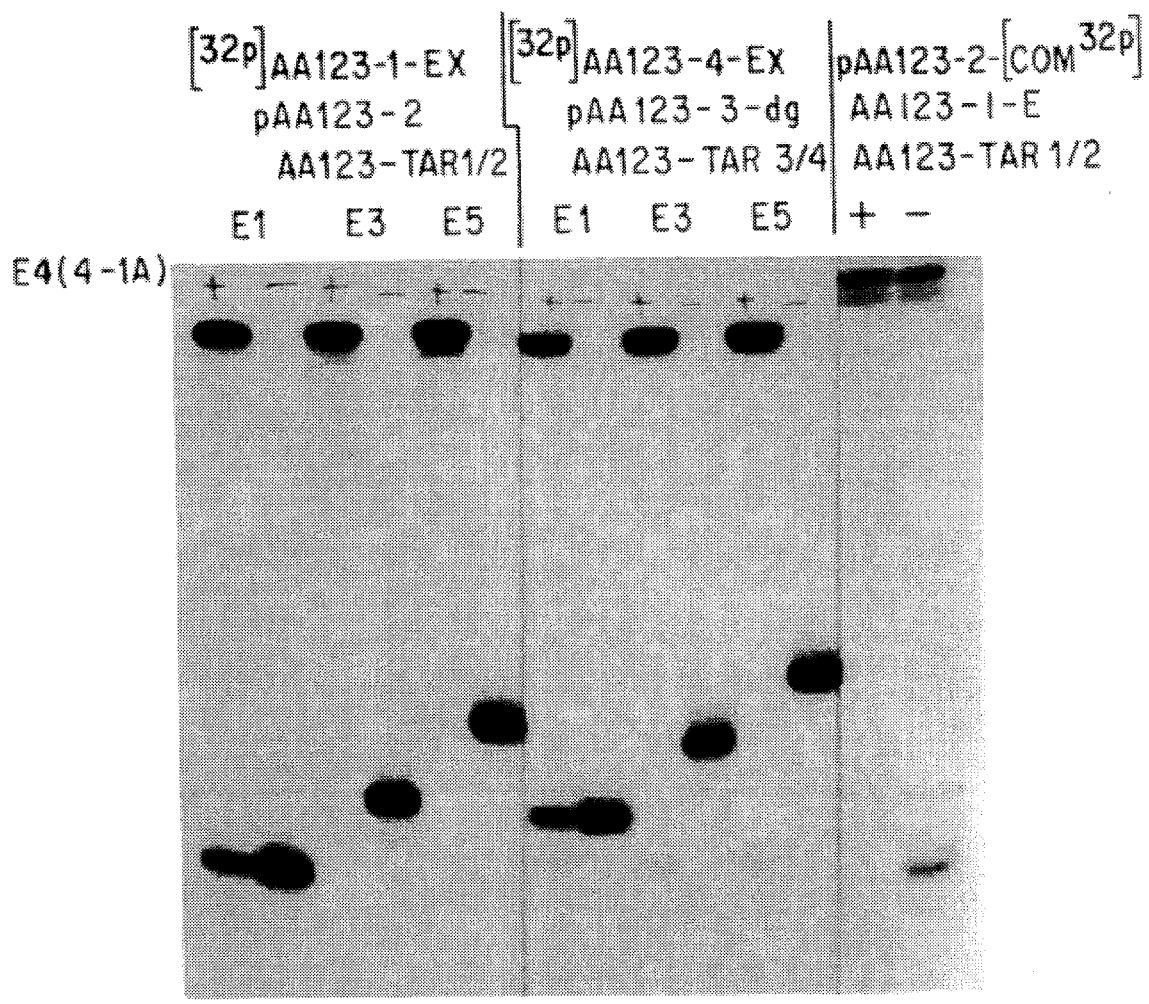
FIG. 4 represents a gel depicting data from example 2.

EXAMPLE 2: Demonstration of Blocking Effect of Abasic Modification on Ligation 3'[$\alpha$-$^{32}$P]-cordycepin labeled AA123-2 was incubated at 50° C. for 40 min with either AA123-1E1, AA123-1E3, or AA123-1E5 (see Table I), the complementary sequence AA123TAR(½)(Table III), and Tth DNA ligase in the presence (+) or absence (−) of Tth endonuclease IV. An identical set of reactions employing the AA123-4E1, AA123-4E3 and AA123-4E5 (Table I) with AA123 TAR(¾) (Table III) and 3'[$\alpha$-$^{32}$P]-cordycepin labeled AA123-3(18) was also performed. The ligated and unligated products were resolved on a 20×40×0.04 cm 12.5% polyacrylamide gel containing 8.3 M urea in 80 mM Tris, 80 mM boric acid pH 8.0, 1.0 mM EDTA. FIG. 4 is an autoradiograph showing that the abasic probes with abasic extensions are not suitable substrates for DNA ligase; and that the blocking extensions are removed by endonuclease IV to render probes −1 and −4 ligatable to probes −2 and −3, respectively. Other data (not shown) confirm the same results are achieved with 3'-PO$_4$ blocking groups and furthermore, the correction and/or ligation of the probes with endonuclease IV and/or DNA ligase occurs only in the presence of the correct complementary sequence.

Examples 3–4, and 8–9 relate to LCR reactions using probes modified to contain abasic sites followed by extensions. Examples 5–7 relate to LCR reactions using probes modified to contain 3' blocking phosphate groups.

EXAMPLE 3: LCR Using One Abasic Site Probe

LCR was performed using probes AA123-1(20), AA123-2 and AA123-3(18) and AA123-4E5 from Table I in a Coy model 50 thermocycler set for 95° C for 30 sec, followed by 55° C. for 110 sec. Reactions were run in 20 µL volume containing 45 mM EPPS pH 7.8, 80 mM KCl, 10 mM MgCl$_2$, 0.5 mM NAD$^+$, 1 mM CoCl$_2$, and 300 ng human placental DNA. Unless otherwise indicated, probes were present at 83 nM (about 5% of probe AA123-2 was 3' end labeled with radioactive [$\alpha$-$^{32}$P]-cordycepin triphosphate to enable detection) and Tth ligase (varying amounts, see data table E-3). Target was zero, $10^2$, $10^3$ or $10^4$ molecules of EcoR1 and PstI digested AA DNA as shown.

The data is presented in Table E-3 below as a signal-to-background ratio. A signal which is consistently at least 3–4 times that of background is generally sufficient to distinguish target from background.

TABLE E-3

| | | Signal-to-Background Ratio | | |
|---|---|---|---|---|
| Fourth Probe | Endo IV Dilution | Cycle No. | $10^3$ Targets | $10^4$ Targets | $10^5$ Targets |
| AA123-4E5 | 1:5000 | 30 | | | 12.0 |
| AA123-4E5 | 1:2000 | 30 | | | 9.7[1] |
| AA123-4E5 | 1:10000 | 30 | | | 22.4[2] |
| AA123-4E5 | 1:50000 | 30 | 1 | 3.5 | 11.6 |
| | | 40 | 3.1 | 6.5 | 9.8 |

TABLE E-3-continued

| | | Signal-to-Background Ratio | | |
|---|---|---|---|---|
| Fourth Probe | Endo IV Dilution | Cycle No. | $10^3$ Targets | $10^4$ Targets | $10^5$ Targets |

[1]Under identical conditions, unmodified probe AA123-4 produced a S/B ratio of only 1.6.
[2]Under identical conditions, probe AA123-4E3 also produced a S/B ratio of 20 at 30 cycles.

EXAMPLE 4: Comparison of Different Abasic Site Probes

Example 3 is repeated, except probe concentration was reduced to 17 nM in a reaction volume of 50 µL, and the fourth probe is either AA123-4E5 or AA123-4E3. The data is shown below, as a signal-to-background ratio.

TABLE E-4

| | | Signal-to-Background Ratio | | |
|---|---|---|---|---|
| Fourth Probe | Endo IV Dilution | Cycle No. | $10^3$ Targets | $10^5$ Targets |
| AA123-4E3 | 1:5000 | 40 | 1 | 6.7 |
| AA123-4E5 | | 40 | 1 | 5.0 |
| AA123-4E3 | 1:10000 | 40 | 1 | 7.7 |
| | | 45 | 1 | 6.2 |
| AA123-4E5 | | 40 | 1 | 11.5 |
| | | 45 | 1 | 5.0 |

EXAMPLE 5: LCR Using One 3' Phosphate Blocked Probe

LCR was performed using probes AA123-1(20), AA123-2, AA123-3(18) and AA 123-4P(22) from Table I under conditions as in Example 3, above. The data is presented in Table E-5 below as a signal-to-background ratio.

TABLE E-5

| | | Signal-to-Background Ratio | |
|---|---|---|---|
| Endo IV Dilution | Cycle No. | $10^3$ Targets | $10^4$ Targets |
| 1:10000 | 28 | 1 | 3.3 |
| | 31 | 2.4 | 5.8 |
| | 34 | 2.3 | 3.8 |
| 1:5000 | 25 | 1 | 1.8 |
| | 28 | 2.0 | 3.8 |
| | 31 | 2.0 | 3.2 |
| | 34 | 1.6 | 2.0 |

EXAMPLE 6: LCR Using Blunt-End 3' Phosphate Blocked Probes

LCR was performed using the blunt-ended, 3'-phosphorylated probe set (see Table I) consisting of AA123-1P(20), AA123-2, AA123-3(20) and AA123-4P(20) in a gL reaction volume containing LCR Buffer supplemented with 50 µg/mL BSA, 0.5 mM CoCl₂ and 300 ng of human placental DNA. Each Probe was present at 83 nM (approximately 5% of probe 2 was 3'-end labeled with [α-$^{32}$P]-cordycepin triphosphate to enable detection) and the enzymes Tth DNA ligase and Tth endonuclease IV were present at 0.15 µg/mL and 4.1 µg/mL respectively. Duplicate reactions for zero, $10^2$, and $10^3$ molecules of target DNA were performed. The samples were overlaid with 15 µL of mineral oil and the temperature cycle consisted of a 95° C. incubation for 30 seconds followed by a 55° C. incubation for 110 seconds. At specified cycles (see Table E-6), 1.4 µL aliquots were removed, mixed with 2.0 µL of stop buffer, heated to 90° C. for 2 min and applied to a denaturing polyacrylamide gel. Table E-6 is the average percent ligated and the ratio of (+)/(−) target for the duplicate reactions. It is observed that 103 targets are distinguishable from zero targets.

TABLE E-6

| | Blunt-End 3'-PO₄ Probes | | |
|---|---|---|---|
| | Percent Ligated (+Target/−Target) | | |
| Cycle No. | 0 Targets | $10^2$ Targets | $10^3$ Targets |
| 31 | 0.91 | 1.90 (2.1) | 2.07 (2.3) |
| 34 | 1.50 | 2.04 (1.4) | 4.24 (2.8) |
| 37 | 2.34 | 4.40 (1.9) | 9.84 (4.2) |

EXAMPLE 7: LCR Using Non-blunt 3' Phosphate Blocked Probes

LCR was performed using the non-blunt probe set (see Table I) consisting of AA123-1P(20), AA123-2, AA123-3(18) and AA123-4P(22) in a 20 µL reaction containing LCR Buffer supplemented with 10 µg/mL BSA, 0.5 mM CoCl₂ and 300 ng of human placental DNA. Each Probe was present at 83 nM (approximately 5% of probe 2 was 3'-end labeled with [α-$^{32}$P]-cordycepin triphosphate to enable detection) and the enzymes Tth DNA ligase and Tth endonuclease IV were present at 0.15 µg/mL and 4.1 µg/mL respectively. Duplicate reactions for zero, $10^2$, and $10^3$ molecules of target DNA were performed. The samples were overlaid with 15 µL of mineral oil and the temperature cycle consisted of a 95° C. incubation for 30 seconds followed by a 55° C. incubation for 110 seconds. At specified cycles (see Table E-5), 1.4 µL aliquots were removed, mixed with 2.0 µL of stop buffer, heated to 90° C. for 2 min and applied to a denaturing polyacrylamide gel. Table E-7 is the average percent ligated and the ratio of (+)/(−) target for the duplicate reactions. It is observed that $10^3$ targets are distinguishable from zero targets.

TABLE E-7

| | Overhang 3'-PO₄ Probes | | |
|---|---|---|---|
| | Percent Ligated (+Target/−Target) | | |
| Cycle No. | 0 Targets | $10^2$ Targets | $10^3$ Targets |
| 28 | 0.75 | 0.88 (1.2) | 2.18 (2.9) |
| 31 | 2.15 | 2.48 (1.2) | 5.66 (2.6) |
| 34 | 4.67 | 6.02 (1.3) | 11.48 (2.5) |
| 37 | 8.21 | 9.45 (1.2) | 16.69 (2.1) |

EXAMPLE 8: LCR Using Probes Modified with an Abasic Site and an Extension of One Base.

LCR was performed using the non-blunt probe set (see Table I) consisting of AA123-1E1, AA123-2, AA123-3(18) and AA123-4E1 in a 20 µL reaction volume containing LCR Buffer supplemented with 50 µg/mL BSA, 0.5 mM CoCl₂ and 300 ng of human placental DNA. Each probe was present at 83 nM (approximately 5% of probe 2 was 3'-end labeled with [α-32P]-cordycepin triphosphate to enable detection) and the enzymes Tth DNA ligase and Tth endonuclease IV were present at 0.15 µg/mL and 41 µg/mL respectively. Duplicate reactions for zero, $10^3$, and $10^4$ molecules of target DNA were performed. The samples were overlaid with 15 µL of mineral oil and the temperature cycle consisted of a 95° C. incubation for 30 seconds followed by a 55° C. incubation for 240 seconds. At specified cycles (see Table E-8), 1.4 µL aliquots were removed, mixed with 2.0 µL of stop buffer, heated to 90° C. for 2 min and applied to a denaturing polyacrylamide gel. Table E-8 is the average percent ligated and the ratio of (+)/(−) target for the duplicate reactions. It is observed that $10^3$ targets are distinguishable from zero targets.

TABLE E-8

| | Abasic Probes with a One Base Extension | | |
|---|---|---|---|
| | | Percent Ligated | |
| Cycle | 0 Targets | $10^3$ Targets | $10^4$ Targets |
| 35 | 0 | 0.98 | 6.99 |
| 40 | 0 | 4.07 | 13.96 |
| 45 | 0 | 6.27 | 19.23 |
| 50 | 0 | 8.74 | 23.50 |

EXAMPLE 9: LCR Using Endonuclease IV Activity Isolated From *Sulfolobus solfataricus*

PART A: Enzyme Isolation: *Sulfolobus solfataricus* (ATCC 35091) was grown as suggested by the ATCC. 20 grams of cells frozen in media were thawed and mixed with 10 mL of 50 mM Tris pH 7.4, 5% (w:v) glycerol, 0.5 mM dithiothreitol to yield a volume of 70 mL. 3.0 mL of 1.0 M Tris pH 7.4 was added and the cells were crushed by two passages through a French press at 14,000 psi. The mixture was centrifuged for 30 min. at 40,000 g. Approximately 66 mL of supernatant was collected, diluted with 0.5 volumes of glycerol and stored at −20° C. 20 mL of the lysate was diluted with 50 mL of 20 mM potassium phosphate pH 7.0, 1.0 mM dithiothreitol, 5% glycerol (v:v) ("Buffer A") and loaded onto a 1.6x9.5 cm column of Blue Sepharose (Pharmacia) equilibrated with Buffer A. The column was washed with 15 mL Buffer A and developed with a linear gradient from 0.1M to 0.74M NaCl in Buffer A. 3.2 mL fractions were collected and 1.25 mL of glycerol were added to each of 45 fractions collected. The fractions were tested for endonuclease IV activity employing the oligonucleotide E4SUB 1 (see Table III) labelled with [$\alpha$-$^{32}$P] cordycepin by terminal deoxynucleotidyl transferase and resolving the cut and uncut oligos on a denaturing polyacrylamide gel. Fractions 27–44 were pooled, made 0.15 mM in $CoCl_2$, and heated to 80° C. for 2.5 min. yielding a final volume of 59 mL. To concentrate the sample it was necessary to remove debris by centrifuging at 28,000 g for 15 min., passing the supernatant through a 0.2 µM filter and finally concentrating 3-fold in an Areicon Centfiprep 10 filter. 3.0 mL of the concentrated protein solution was diluted with 30.0 mL of 25 mM Tris pH 7.4, 1.0 mM $MgSO_4$, 50 µM $CoCl_2$ and 5% (v:v)glycerol ("Buffer B") and loaded onto a 4.0 mL heparin-agarose column equilibrated with Buffer B. The column was developed using a gradient of 0.25 M to 0.5 M KCl in Buffer B collecting 1.0 mL fractions. Fractions were assayed for abasic nuclease activity and fractions 9–11 were pooled. The 3.0 mL were transferred to 25 mM EPPS pH 7.7, 0.1 M KCl, 1 mM $MgCl_2$, 50 µM $CoCl_2$ and 5% (v:v) glycerol ("Buffer C") by passing the sample over a BioRad 10DG column equilibrated with Buffer C. 4.0 mL was collected and concentrated to ca. 100 µL in an Amicon Centriprep 10.

This sample was heated to 90° C. for 5 min and was found to be free of both single- and double-stranded nuclease activity using oligodeoxyribonucleotides AA250-1 and AA250-3 as substrates.

PART B: LCR Reactions: LCR was performed comparing the blunt-ended probe set consisting of AA250-1, AA250-2, AA250-3(24) and AA250-4(19) with the non-blunt probe set with one abasic probe consisting of AA250-1E5, AA250-2, AA250- 3(22) and AA250-4(21 ) in a 20 µL reaction volume containing LCR Buffer supplemented with 10 µg/mL BSA, 2.0 mM $CoCl_2$ and 300 ng of human placental DNA. Each probe was present at 83 nM (approximately 5% of probe 2 was 3'-end labeled with [$\alpha$-$^{32}$P]-cordycepin triphosphate to enable detection) and the Tth DNA ligase was present at 0.15 µg/mL. The purified *Sulfolobus solfataricus* endonuclease IV activity was used at a final dilution of 1:10. Duplicate reactions for zero and $10^6$ molecules of target DNA were performed for both blunt and non-blunt probe sets. The samples were overlaid with 15 µL of mineral oil and the temperature cycle consisted of a 95° C. incubation for 30 seconds followed by a 55° C. incubation for 60 seconds. At specified cycles (see Table E-9), 1.4 µL aliquots were removed, mixed with 2.0 µL of stop buffer, heated to 90° C. for 2 min and applied to a denaturing polyacrylamide gel. Table E-9 gives the average percent ligated and the ratio of $10^6$ targets/zero targets for the duplicate reactions in each case. It is observed that the ratio of $10^6$ targets/zero targets is better with the abasic extension modified non-blunt probe set. This improvement is due to a decrease in the signal arising in the reactions containing zero target molecules whereas the percent ligated in the reactions containing $10^6$ target molecules is the same for both probe sets.

TABLE E-9

| LCR with Endo IV from *Sulfolobus solfataricus* | | | |
|---|---|---|---|
| Cycle No. | 4th Probe | 0 Targets | $10^6$ Targets | Ratio (+/−) Target |
| 30 | AA123-1 | 3.9 | 24.1 | 6.2 |
| 30 | AA123-1E5 | 0.5 | 26.1 | 54.0 |
| 35 | AA123-1 | 6.8 | 38.0 | 5.6 |
| 35 | AA123-1E5 | 3.1 | 35.8 | 11.7 |
| 40 | AA123-1 | 18.7 | 51.1 | 2.7 |
| 40 | AA1E5 | 15.3 | 52.8 | 3.5 |

Examples 10–13 relate to the effect of divalent cations on LCR and Endonuclease IV modified LCR.

EXAMPLE 10: Effect of $MnCl_2$ on LCR and the Improvement with Endonuclease IV

LCR was performed using the non-blunt probe set (see Table I) consisting of AA123-1P(20), AA123-2, AA123-3(18) and AA123-4P(22) in a 20 µL reaction volume containing LCR Buffer supplemented with 10 µg/mL BSA, 0.1 mM $MnCl_2$ and 300 ng of human placental DNA. In this experiment probe AA123-1P(20) was haptenated with biotin at its 5' terminus and AA123-2(20) was haptenated at its 3' terminus with digoxigenin for a purpose not related to this experiment. Each probe was present at 83 nM (approximately 5% of probe 3 was 3'-end labeled with [$\alpha$-$^{32}$P]-cordycepin triphosphate to enable detection) and the enzymes Tth DNA ligase and Tth endonuclease IV were present at 0.15 µg/mL and 4.1 µg/mL respectively. Duplicate reactions for zero and $10^3$ molecules of target DNA were performed. The samples were overlaid with 15 µL of mineral oil and the temperature cycle consisted of a 95° C. incubation for 30 seconds followed by a 55° C. incubation for 110 seconds. At specified cycles (see Table E-10), 1.4 µL aliquots were removed, mixed with 2.0 µL of stop buffer, heated to 90° C. for 2 min and applied to a denaturing polyacrylamide gel. Table E-10 gives the average percent ligated and the ratio of (+)/(−) target for the duplicate reactions. It is observed that $10^3$ targets are not distinguishable from zero targets.

TABLE E-10

Overhang 3'-PO$_4$ Probes with MnCl$_2$

| | Percent Ligated | | |
|---|---|---|---|
| Cycle No. | 0 Targets | $10^3$ Targets | Ratio (+/−) Target |
| 25 | 3.29 | 2.47 | 0.8 |
| 35 | 23.65 | 23.30 | 1.0 |

EXAMPLE 11: Effect of CoCl$_2$ Concentrations on LCR with Unmodified, Non-blunt Probes LCR was performed using the unmodified, non-blunt probe set (see Table I) consisting of AA123-1(20), AA123-2, AA123-3(18) and AA123-4 (22) in a 20 µL reaction volume containing LCR Buffer supplemented with various amounts of CoCl$_2$ as indicated in Table E-11, 10 µg/mL BSA and 300 ng of human placental DNA. In this experiment probe AA123-1P(20) was haptenated with biotin at its 5' terminus and AA123-2(20) was haptenated at its 3' terminus with digoxigenin. Each probe was present at 83 nM (approximately 5% of probe 3 was 3'-end labeled with [α-$^{32}$P]-cordycepin triphosphate to enable detection) and the final concentration of Tth DNA ligase equalled 0.15 µg/mL. Duplicate reactions containing either zero or $10^6$ molecules of target DNA were performed. The samples were overlaid with 10 µL of mineral oil and the temperature cycle consisted of a 95° C. incubation for 30 s followed by a 55° C. incubation for 110 s. At 20 and 30 cycles 1.4 µL aliquots were removed, mixed with 2.0 µL of stop buffer, heated to 90° C. for 2 min and applied to a denaturing polyacrylamide gel. Table E-11 is the average percent ligated and the ratio of (+)/(−) target for the duplicate reactions. It is observed that CoCl$_2$ has an inhibitory effect on the extent of amplification in the reactions both with and without target DNA. This implies that CoCl$_2$ has an inhibitory effect on Tth DNA ligase.

TABLE E-11

Effects of CoCl$_2$ Concentration on LCR

| | | Percent Ligated | | |
|---|---|---|---|---|
| Cycle No. | CoCl$_2$ (mM) | 0 Targets | $10^6$ Targets | Ratio (+/−) Target |
| 20 | 0.0 | 0.19 | 4.60 | 24.2 |
| | 0.5 | 0.32 | 3.13 | 9.8 |
| | 1.0 | 0.37 | 0.90 | 2.4 |
| | 2.0 | 0.0 | 0.0 | N.A. |
| 30 | 0.0 | 12.28 | 22.42 | 1.8 |
| | 0.5 | 2.68 | 12.96 | 4.8 |
| | 1.0 | 0.75 | 5.88 | 7.8 |
| | 2.0 | 0.0 | 0.0 | N.A. |

EXAMPLE 12: LCR with Modified and Unmodified Probes in the Absence of MgCl$_2$ and CoCl$_2$ LCR was performed in a buffer containing 47 mM EPPS pH 7.8, 80 mM KCl, 10 mM NH$_4$Cl$_2$, 5 mM MnCl$_2$, 10 µg/mL BSA and 15 µg/mL human placental DNA and no MgCl$_2$ or CoCl$_2$. Four sets of probes were used in this experiment, representing 3'-phosphorylated ends, abasic sites with extensions of 3 or 5 bases, and no modifications, as follows (see Table I):

| | |
|---|---|
| unmodified, non-blunt set | AA123-1(20), AA123-2, AA123-3(18), and AA123-4(22) |
| 3'-phosphorylated set | AA123-1P(20), AA123-2, AA123-3(18), and AA123-4P(22) |
| abasic extension set | AA123-1E3, AA123-2, AA123-3(18), and AA123-4E3 |
| abasic extension set | AA123-1E5, AA123-2, AA123-3(18), and AA123-4E5 |

Duplicate reactions containing either zero or $10^4$ molecules of target DNA were performed. The samples were overlaid with 15 µL of mineral oil and the temperature cycle consisted of a 95° C. incubation for 30 s followed by a 55° C. incubation for 110 s. After 60 cycles 3.0 µL aliquots were removed, mixed with 3.0 µL of stop buffer, heated to 90° C. for 2 min and applied to a denaturing polyacrylamide gel. No amplification occurred with any of the probe sets indicating that MnCl$_2$ at 5 mM cannot substitute for 10 mM MgCl$_2$ supplemented with low concentrations of either CoCl$_2$ or MnCl$_2$.

Analogous LCR assays incorporating the same buffer as above but with 10 mM MnCl$_2$ and an unmodified probe set consisting of AA123-1(20), AA123-2, AA123-3(18) and AA123-4(22) also showed no amplification out to 44 cycles.

EXAMPLE 13: LCR and Endo IV LCR with varying Cobalt Concentrations.

Endo IV-LCR assays were performed in a reaction mix consisting of 50 mM EPPS pH 7.8, 5mM MgCl$_2$, 20µg/ml BSA, 1×10$^{12}$ of the oligos given in Table IV below, 215 units *Thermus thermophilus* DNA ligase, a 1.5×10$^{-4}$ dilution of *T. thermophilus* endonuclease IV, and various concentrations of CoCl$_2$ ranging from 500µM to 2 mM in a final reaction volume of 20 microliters. The oligos are specific for positions 6693–6739 of the *Chlamydia trachomaas* cryptic plasmid as given by Hatt, C. et al. *Nuc. Acids Res.* 16:4053–4067 (1988). Oligos #1 and #4 include 3' phosphate blocking groups as shown.

TABLE IV

DNA PROBE SETS TO Position 6693–6739 of *Chlamydia trachomatis* cryptic plasmid

| Designation | SEQUENCE | | SEQ ID No. |
|---|---|---|---|
| #1 | 5' Fl-GATACTTCGCATCATGTGTTCCp | 3' | 35 |
| #3 | 5'                pGGAGTTTCTTTGTCCTCCTATAACG-Bio | 3' | 36 |
| #2 | 3' Fl-CTATGAAGCGTAGTACACAAGGp | 5' | 37 |
| #4 | 3'               pCCTCAAAGAAACAGGAGGATATTGC-Bio | 5' | 38 | where: p = 3' - phosphate blocking group; and p = a normal 5' phosphate group; Fl = a fluorescein moiety; and Bio = a biotin moiety Endo IV-LCR cycling conditions were 95° C. for 30 seconds then 55° C. for 110 seconds repeated thirty times in a Coy thermocycler. Negative reactions were set up with 300 nanograms of human placental DNA in dH$_2$O. Positive reactions contained either $10^4$ or $10^6$ molecules of a synthetic DNA oligonucleotide corresponding to map positions 6693–6739 of the *C. trachomatis* plasmid sequence in a background of 300 ng of placental DNA. Following amplification, reactions were diluted 1:1 with IMx diluent buffer, and the LCR amplification products were detected via a sandwich immunoassay performed using the Abbott IMx® automated immunoassay system. Results are shown in Table E-13 below. It can be seen that at cobalt concentrations of 1.0 mM or less, $10^6$ targets are distinguishable from no target; while at greater cobalt concentrations, target was not distinguishable.

TABLE E-13

| Amount of Target | IMx rate count | | |
|---|---|---|---|
| | CoCl$_2$ concentration | | |
| | 0.5 mM | 1 mM | 2 mM |
| 0 | 27.8 | 8.8 | 23.5 |
| $10^4$ | 47.3 | 8.9 | 19.8 |
| $10^6$ | 390.0 | 71.5 | 16.3 |

Examples 14–17 relate to the use of LCR reactions using endonuclease IV correctable modified probes which also contain ribonucleotide residues. The ribonucleotide residues permit selective destruction of the amplification products using RNase or alkali as a means for controlling possible contamination, as is taught in WO91/17270 for conventional LCR reactants. The probes used in these examples are shown in Table V below.

EXAMPLE 14: Preparation of Mixed Ribo- and Deoxyribo-Oligonucleotides Having 3' Phosphate Blocking Groups The mixed ribo- and deoxyribo-oligonucleotides AA 123-1R and AA123-4R (see Table V) were prepared by initiating synthesis on a solid phase support beating an adenosine ribonucleotide. Synthesis was continued with the sequential addition of deoxyribonucleotide phosphoramidites using an automated DNA synthesizer. The resulting mixed oligonucleotide "ribo-modified" probe) was cleaved from the support and deprotected with 37% NH$_4$OH at 55° C. for 12 hours and purified by reverse-phase HPLC on a C18 column.

Radioactive phosphate moieties were added in two steps to make oligodeoxyribonucleotides having at the 3' terminal residue a 2'-OH and 3'-$^{32}$PO$_4$ group. First, the ribo-modified probes AA123-1R or AA123-4R were incubated for 1.5 h at 37° C. with 20 pmol of [α-$^{32}$P]-cordycepin 5'-triphosphate (5000 Ci/mmol) and 10 units of deoxynucleotidyl terminal transferase in a total reaction volume of 15 μL buffered with 140 mM sodium cacodylate pH 7.2, 1 mM CoCl$_2$, 0.1 mM dithiothreitol. The unreacted cordycepin was separated from the oligonucleotide on a 1.0 mL Sephadex Go50 column equilibrated with 5 mM Tris pH 8.0, 0.1 mM EDTA. Two drop fractions (ca. 75 μL) were collected and the elution profile was monitored by counting 1.0 μL of each fraction in 4.0 mL of liquid scintillation cocktail. The fractions containing the oligonucleotide were pooled. The resulting oligonucleotide contains a single $^{32}$P-labeled 3'-phosphodiester bond adjacent to the unique 2'-OH group at the 3' terminus.

Second, the phosphodiester bond between the oligonucleotide and the cordycepin was cleaved with T2 RNase, which cuts 3' to the adenosine residue, liberating the cordycepin deoxyribonucleoside and the desired fibo-modified probes. Approximately 0.2 pmol of $^{32}$P labeled AA 123-1R or AA 123-4R were incubated with 2.5 units of T2 RNase for 1 h

TABLE V

Mixed DNA/RNA PROBE SETS TO Position 123 of *ACTINOBACILLUS ACTINOMYCETEMCOMITANS*

| Designation | SEQUENCE | | SEQ ID No. |
|---|---|---|---|
| AA123-1R (20) | 5'TTGTCGAGCACCTTGAATAA | -3' | 25 |
| AA123-1RP (20) | 5'TTGTCGAGCACCTTGAATAAp | -3' | 26 |
| AA123-2 | 5'              pTTAATGGCTTCGATTGGGCT-3' | | 6 |
| AA123-3 (20) | 3'AACAGCTCGTGGAACTTATTp | -5' | 7 |
| AA123-4R (20) | 3'            AATTACCGAAGCTAACCCGA-5' | | 27 |
| AA123-4RP (20) | 3'          pAATTACCGAAGCTAACCCGA-5' | | 28 | where: A is adenosine ribonucleotide; p = 3' - phosphate blocking group; and p = a normal 5' phosphate group.

at 37° C. in a total reaction volume of 4.0 μL buffered with 50 mM potassium acetate, pH 5.2. The reaction was terminated by adding 5.0 μL of stop buffer and 1.0 μL of 5' LCR buffer and 5.0 μL was loaded on a 20×40×0.04 cm denaturing 12.5% polyacrylamide gel and electrophoresed for 1.75 h at 30W. As can be observed in FIG. 5 (lanes 3 and 11), the products AA 123-1RP(20) and AA123-4RP(20), resulting from RNase digestion of the [α-$^{32}$P]-cordycepin labeled AA 123-1R and AA 123-4R migrate faster than the undigested oligonucleotides (lanes 2 and 10). Although the products of digestion with T2 RNase are expected to be decreased in length by only one base, they are observed to migrate with an Rf value similar to that of the faint failure sequence that is two bases shorter than the undigested material. This is expected since the correlation between length and Rf values of DNA fragments is based on all the DNA fragments having the same mass to charge ratio but, the additional negative charge associated with the 3'-phosphorylated oligonucleotide will increase the charge to mass ratio, resulting in an increased Rf value.

EXAMPLE 15: Activity of Endonuclease IV on Ribo-Modified Probes

Figure 5:
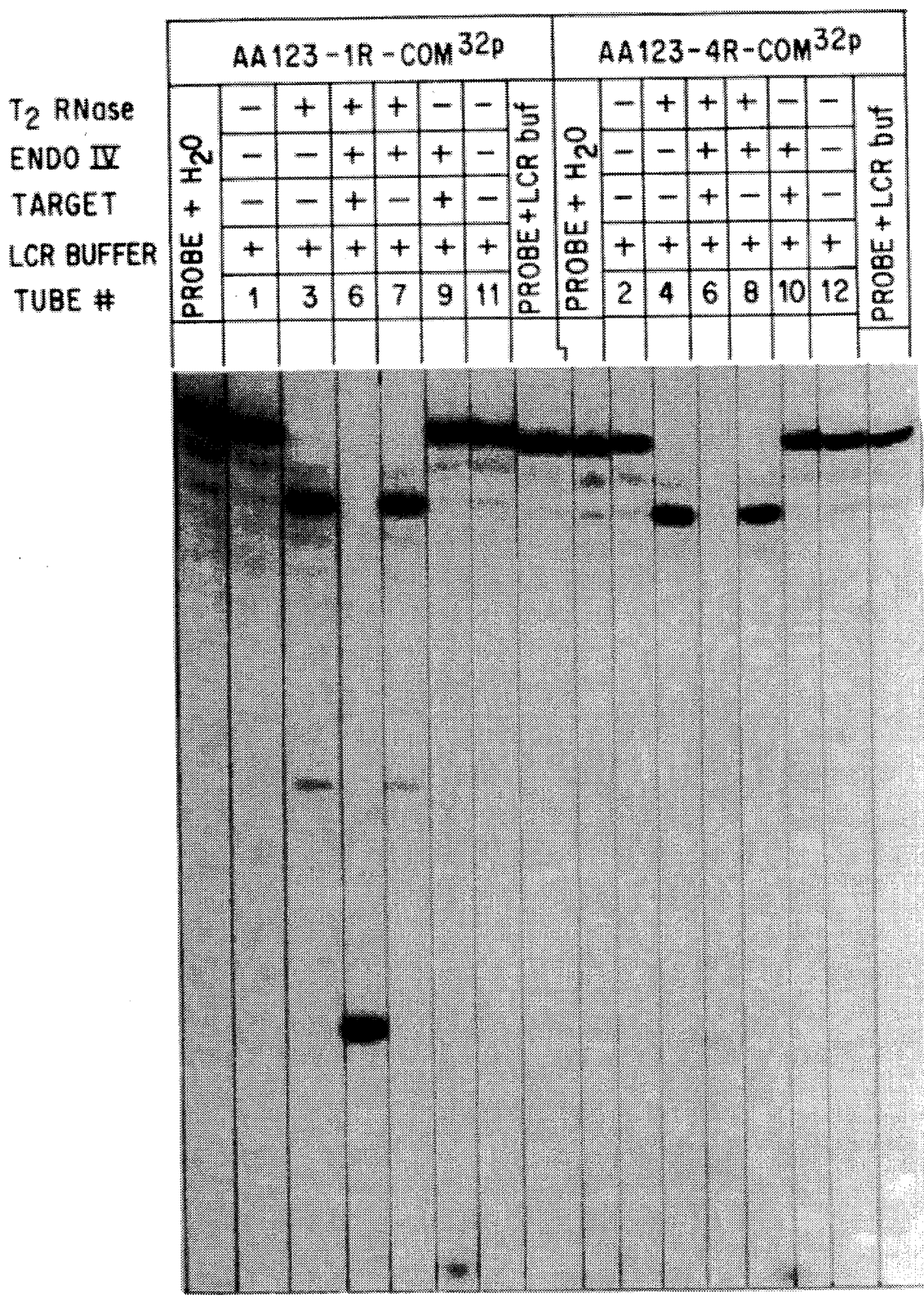
FIG. 5 represents a gel depicting data from examples 14 and 15.

The 3'-phosphorylated oligonucleotides AA123-1RP(20) and AA123-4RP(20) were further analyzed to determine if the 3'-PO$_4$ group attached to a ribonucleoside could be removed by Tth endonuclease IV, and if the enzymatic removal required that AA 123 1RP(20) and AA 123-4RP(20) be hybridized to the complementary synthetic target oligonucleotides AA 123TAR(½) or AA 123TAR(¾), respectively, (see Table III) so that the 3'-PO$_4$ is located in a double-stranded region. This was achieved by digesting aliquots of the [α-$^{32}$P]-cordycepin labeled AA123-1R and AA123-4R with T2 RNase, as in example 14, followed by a second digestion with Tth endonuclease IV in the presence or absence of AA123TAR(½) or AA123TAR(¾) in LCR buffer. As required, 1.7 pmol of AA123TAR(½) or AA123TAR(¾) and Tth endonuclease IV, to a final concentration equal 4.1 μg/mL, were added and the volume was adjusted to 10 μL with water. The samples were incubated for 1 h at 55° C., 5.0 μL aliquots were removed into 5.0 μL of stop buffer, and then analyzed by denaturing polyacrylamide gel electrophoresis as detailed above. As can be seen in FIG. 5 (lanes 4 and 12), the removal of the 3'-$^{32}$PO$_4$ from the oligonucleotide occurs only when T2 RNase, Tth endonuclease IV and the strand complementary to the labeled oligonucleotide are all present. The absence of any one of these three materials prevents the removal of the $^{32}$P label from AA123-1RP(20) and AA 123-4RP(20).

It has also been observed (data not shown) that the cleavage of AA123-1RP(20) by T2 RNase in the presence of target AA123TAR(½) but the absence of Tth endonuclease IV results in the same size product as observed with T2 RNase in the absence of the complementary target. These results demonstrate the reaction product from T2 RNase treatment of the [α-$^{32}$P]-cordycepin labeled oligonucleotide, which should be a 3'-PO$_4$ group, is indeed a suitable substrate for endonuclease IV and obeys the same double-stranded substrate specificity described for endonuclease IV with DNA substrates.

EXAMPLE 16: Demonstration of Ligation of Endonuclease IV Product

Part A. 3'phosphorylated probes were synthesized by initiating automated synthesis with 2-[[2-( 4,4'-dimethoxytrityl)oxy]ethyl] sulfonyl]ethyl 2-cyano-ethyl N,N-diisopropylphosphoramidite (Horn, T and Urdea, M *Tet. Lett.* 27 4705+ (1986)) as reported (Ashely, GW and Kushland, DM *Biochemistry* 30:2927–2933 (1991)), followed by the sequential addition of ribonucleotide and deoxyribonucleotide cyanoethyl phosphoramidites using an automated DNA synthesizer. The oligonucleotide was cleaved from the support and deprotected with 37% NH$_4$OH at 55° C. for 12 h and purified by reverse-phase HPLC. on a C18 column.

Figure 6:
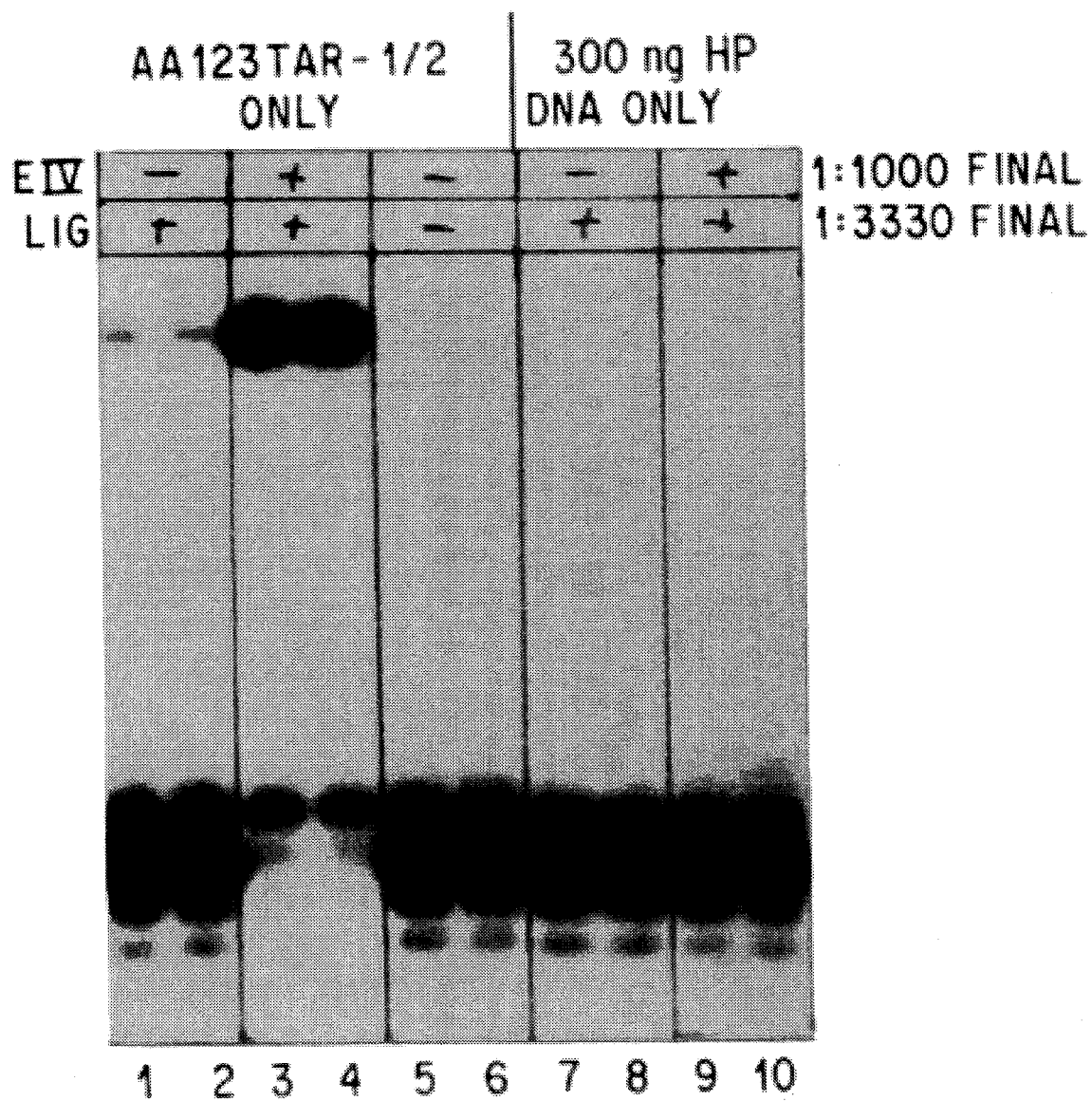
FIG. 6 represents a gel depicting data from example 16.

Part B. It was then demonstrated that when the 3'-phosphate is removed by Tth endonuclease IV (as in example 15) the resulting ribo-modified oligonucleotide is a suitable substrate for ligation by Tth DNA ligase. Duplicate reactions containing 83 nM AA123-1RP(20) from example 14, 16 nM AA 123-2 (approximately 25% 3'-labeled with α-$^{32}$P]-cordycepin triphosphate), and 66 nM AA123TAR(1/2) in LCR Buffer supplemented with 2.0 mM CoCl$_2$ and 10 μg/mL BSA were incubated in the presence or absence of 0.15 μg/mL Tth DNA ligase and/or 4.1 μg/mL Tth endonuclease IV at 55 ° C. for 1 h. Analogous assays containing 300 ng of human placental DNA and no AA 123TAR(½) were also performed. As can be observed in FIG. 6 (lanes 3 and 4), almost all of the AA 123-2 is convened into a ligated product only when Tth endonuclease IV, Tth DNA ligase and AA123TAR(½) are all present.

It was also observed (FIG. 6, lanes 1 and 2) that a small amount of ligated product was formed in the presence of AA123TAR(½) and ligase but the absence of Tth endonuclease IV. The formation of a ligated product in the absence of Tth endonuclease IV implies that the 3' position of AA 123-1RP is not completely blocked with a 3'-PO4 group. A 3'-OH group may arise from incomplete 3'-phosphorylation during synthesis or the removal of and/or exchange of the 3'-PO$_4$ group with the 2'-OH group during the treatment with strong alkali that follows synthesis. If the exchange reaction is responsible for generating an unblocked 3'-OH group then it must be possible for Tth DNA ligase to use the 2'-PO$_4$, 3'-OH ribonucleoside as a substrate.

EXAMPLE 17: LCR Using Modified Probes Containing a 3'Ribonucleotide Bearing a 3' Phosphate LCR was performed using the blunt-end probe set (see Table V) consisting of AA123-1RP(20), AA123-2, AA123-3(20) and AA123-4RP(20) in a 20 μL reaction volume containing LCR Buffer supplemented with 10 pg/mL BSA, 0.5 mM CoCl$_2$ and 300 ng of human placental DNA. Each probe was present at 83 nM (approximately 5% of probe 2 was 5'-end labeled with [γ-$^{32}$P]-adenosine triphosphate to enable detection) and the enzymes Tth DNA ligase and Tth endonuclease IV were present at 0.15 μg/mL and 4.1 μg/mL, respectively. Duplicate reactions for zero, 10$^3$, and 10$^4$ molecules of target DNA were performed. The samples were overlaid with 15 μL of mineral oil and the temperature cycle consisted of a 95° C. incubation for 30 seconds followed by a 55° C. incubation for 110 seconds. At specified cycles (see Table E-17), 1.7 μL aliquots were removed, mixed with 2.5 μL of stop buffer, heated to 90° C. for 2 min and applied to a denaturing polyacrylamide gel. Table E-17 gives the average percent ligated and, in parentheses, the ratio of (+)/(−) target for the duplicate reactions. It is observed that 10$^3$ targets are distinguishable from zero targets.

TABLE E-17

LCR with 3'-Ribo; 3'-PO$_4$ Probes

| Cycle No. | Percent Ligated (+Target/−Target) | | |
|---|---|---|---|
| | 0 targets | 10$^3$ targets | 10$^4$ targets |
| 28 | 0.45 | 1.65 (3.7) | 5.87 (13.0) |
| 31 | 1.83 | 5.50 (3.0) | 12.08 (6.6) |
| 34 | 6.70 | 12.87 (1.9) | 21.60 (3.2) |
| 37 | 13.35 | 23.39 (1.8) | 28.49 (2.1) |

For Examples 18 and 19 plasmid pUC19 is used as target, hence the designation "pUC" in Table VI, below. The next numeral (after the dash) designates the position of the probe in a set of four: Probes numbered −1 and −2 have the same 5'-3' orientation while probes numbered −3 and −4 have the opposite sense. Probes numbered -1 and -3 hybridize, as do probes numbered −2 and −4. "P" and "p" indicate a phosphate group. This is normal and required on a 5' terminus, but serves as a ligation blocking modification on a 3' end. "E" and "x" designate an abasic site (described further below). A number "1" following the "E" designates the length of complementary bases (overhang) beyond the abasic site.

TABLE VI pUC19 Modified Probes

| Designation | SEQUENCE & ORIENTATION | | SEQ ID No. |
|---|---|---|---|
| pUC-1P | 5'-AATTCGAGCTCGGTACCCp | -3' | 29 |
| pUC-1E1 | 5'-AATTCGAGCTCGGTACCCxG | -3' | 30 |
| pUC-2 | 5'- pGGGGATCCTCTAGAGTCGACCTGCA-3' | | 31 |
| pUC-3 | 3'-GCTCGAGCCATGGGp | -5' | 32 |
| pUC-4P | 3'- pCCCCTAGGAGATCTCAGCTG-5' | | 33 |
| pUC-4E1 | 3'- GxCCCCTAGGAGATCTCAGCTG-5' | | 34 |

EXAMPLE 18: LCR Using a pUC19 Target with 3' Phosphate Blocked Probes

A probe set is designed to detect the pUC19 target sequence by LCR, with reduced background levels. The probe set (see Table VI) features two normal probes (pUC-2 and pUC-3) two probes (pUC-1P and pUC-4P) containing terminal 3' phosphate blocking groups.

LCR reactions are performed (substantially as described herein) using various amounts of target (pUC19). After the hybridization step of each cycle, endonuclease IV purified from *E. coli* is added to the reaction. This can be done under standard LCR conditions, since *E. coli* endonuclease IV is somewhat thermostable. Alternatively, endonuclease IV from a thermostable species such as *Thermus thermophilus* could be used. As a control, the LCR is run using the same number of target molecules without the addition of endonuclease IV. In these controls a probe set similar to the one shown above is used, only the 3' terminal nucleotides (containing the 3' phosphates) are not included on probes −1 and −4.

In both the experimental and control reactions, the rate of appearance of ligated product is correlated with the initial number of target molecules added. What distinguishes the two protocols is that in the second case, a "blank" tube containing no target molecules will give rise to signal at about the same rate as a tube containing 1000 target molecules, whereas in the case where modified probes and endonuclease IV are used, a "blank" tube containing no target molecules will give rise to signal significantly more slowly than does a tube containing 1000 target molecules. This suppression of background provides an advantage in increasing the usable range of sensitivity of the assay.

Those skilled in the art will immediately appreciate the desirability of employing a highly thermostable endonuclease IV, for the same reasons that highly thermostable ligases and polymerases are useful and desirable in LCR and PCR, respectively. Those skilled in the art will also appreciate that other enzymes, either known or not yet known, which can remove modifications at the 5' or 3' ends of a DNA strand in a template dependent manner leaving the previously blocked 5' phosphate or Y hydroxyl intact, can be employed in a manner completely analogous to endonuclease IV as described above.

EXAMPLE 19: LCR Using a pUC19 Target with Abasic Probes

A probe set is designed to detect the pUC19 target sequence by LCR, with reduced background levels. The probe set (see Table VI) features two normal probes (pUC-2 and pUC-3) and two modified probes (pUC-1E1 and pUC-4E1 ) containing a Y end abasic site followed by one additional normal residue complementary to the target.

LCR reactions are performed as in example 18. Results and interpretation will be similar to those of example 18.

The following text and renumbered examples are incorporated herein from U.S. Ser. No. 07/860,861 or 07/869,306, which are now published as WO93/20191.

Reagents & Enzymes

Media for the growth of bacteria were purchased from Difco (Detroit, Mich., USA) or Gibco (Madison, Wisc. USA). Restriction enzymes, T4 DNA ligase, T4 DNA polymerase, large fragment of the enzyme *E. coli* DNA polymerase I and Polynucleotide kinase were purchased from Bethesda Research Laboratories (BRL, Gaithersburg, Md. USA); New England Biolabs (Beverley, Mass. USA); Boehringer Mannhelm (Indianapolis, Ind. USA) or PL Laboratories (Milwaukee, Wisc. USA). Agarose was from International Biotechnology, Inc. Kanamycin was purchased from Sigma. X-gal (5-bromo-4-chloro-3-indoyl- D-galactoside) was purchased from BRL. *E. coli* K12 strains HB101, DH5a, *E. coli* K12/pUC9, *E. coli* K12/pUC19, and *E. coli* K12/pBR322 are obtainable from BRL or PL Laboratories.

Buffers are defined as follows:
TAE (Tris-acetate) defined as 40 mM Tris, 20 mM acetic acid, 2 mM EDTA; LB broth defined per liter as 10g BactoTryptone, 5 g yeast extract, 5 g NaCl; TB top agar defined as LB broth, defined supra, containing 0.75 % w/v agar, 5 mM calcium chloride, 0.2% glucose, 10 mM magnesium sulfate; TE defined as 10 mM Tris·Cl and 1 mM EDTA; 5 X LCR buffer defined as 50 mM EPPS/K+ pH 7.6, 10 mM NH$_4$Cl, 10 mM MgCl$_2$, 80 mM KCl, 100 μg/ml gelatin, and 0.5 mM CoCl$_2$; and SOC. media defined as 20 g bactotryptone, 5 g yeast extract, 0.5 g NaCl, 2.5 mM KCl, 10 mM MgCl$_2$, 20 mM glucose, pH 7.0

Example 20: Synthetic Abasic Substrates Which are Suitable in an Assay for Class II AP Endonuclease Detection.

Synthetic substrates comprising hairpin structures containing a synthetic abasic site in the double stranded region of the hairpin were synthesized by known methods in phosphoramidite chemistry on a DNA synthesizer. The substrates (a) are small in size so that they can easily be synthesized in high yield and efficiency; (b) have a single abasic site incorporated using standard DNA synthesis chemistry; (c) have the abasic site modified by a (reduced) furan ring which precludes cleavage by a general base-catalyzed β-elimination mechanism ( Eritja, et al., *Nucleosides and Nucleotides* 6 (4): 803–814 (1987); (d) result in an easily resolvable cleavage product; (e) have a free 3' hydroxyl group for labelling using commercially available [$^{32}$P]- labelled nucleotides and terminal transferase; and (f) contain palindromic sequences which cause the formation of a hairpin.

The hairpin serves two functions. Firstly, it obviates the need for a hybridization step before the oligonucleotide can be used. Secondly, the hairpin also has a high melting temperature, which is generally much higher than two oligonucleotides of equal double stranded region. This is important for use at high temperatures with thermophilic enzymes. Previous synthetic substrates were composed of two obligatorily separate oligonucleotides. The two strands needed to be kept separate by the need to depurinate a single purine residue in a polypyrimidine strand prior forming a double-stranded DNA molecule, with a complementary purine-containing strand. The latter (purine-containing) strand would need to be kept separate from the strand undergoing treatment to depurinate.

Two hairpin substrates of the present invention are exemplified as follows:

Hairpin 1 is a 39-residue oligonucleotide ( wherein X is an abasic residue) having the following structure:

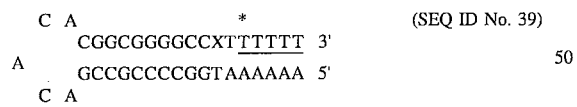

(SEQ ID No. 39)

Upon cleavage by class II AP endonuclease, the substrate yields a 7-residue nucleotide product (one nucleotide is actually the abasic residue).

Hairpin 2 is a 45-residue oligonucleotide ( wherein X is an abasic residue) having the following structure:

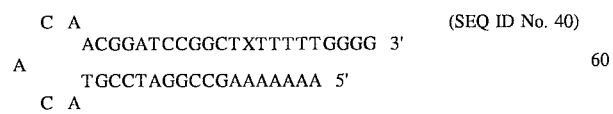

(SEQ ID No. 40)

Upon cleavage by class II AP endonuclease, the substrate yields a 10-residue nucleotide product.

The melting temperatures of the hairpin substrates of the present invention at 3 μM in 25 mM EPPS pH 7.6, 0.1 M NaCl, 10 mM EDTA were determined to be approximately 81° C. (hairpin 1) and approximately 74° C. (hairpin 2).

Both hairpins have design features to minimize 3' exonuclease activity of the type exhibited by *E. coli* exonuclease III. Endonuclease IV activity in *E. coli* is heat stable at 65° C., whereas exonuclease III activity is not, and this property is exploited to assay the former in the presence of the latter. Hairpin 1 has 5 phosphorothioate linkages between the six 3' terminal thymidines. These linkages have been shown to resist the action of exonuclease III. Hairpin 2 has a 4 nucleotide extension at the 3' end. It has been shown that exonuclease III, which requires double stranded DNA, will not act on a substrate with a 4 nucleotide overhang at the 3' end. Cleavage of these substrates was not observed on treatment with 0.2 M NaOH for 15 min at 37° C. indicating that the synthetic abasic site was stable as predicted.

The hairpin oligonucleotides are used as substrates in the assay described herein for the thermophilic class II AP endonuclease of the present invention. An aliquot of the EPPS-containing buffer, along with the hairpin substrate, is warmed at 50° C. for > 1 min prior to starting the assay by addition of enzyme. The enzyme is incubated for a pre-determined time ranging from about 5–30 min for crude and partially purified extracts and up to 19 h for screening of clone banks, and the assay stopped by addition of 20 μl of formamide-dye mix. After heating for about 2 min at 95°–100° C., aliquots of about 10–16 ml are loaded on a 20% acrylamide/50% w/v urea/TBE gel (15 cm H×17 cm W×0.7 mm thick) and substrates and products localized by electrophoresis at 55 V/cm (800 V for 15 cm gel) until the Bromophenol blue dye is approximately at the bottom of the gel (about 30–45 min). An aluminum plate is fastened to the exposed glass plate to uniformly spread and dissipate heat generated during electrophoresis.

When the gel is finished, it is removed from the plates onto a used piece of film, and covered with plastic film, e.g. Saran wrap. The enzyme is then localized by autoradiography. For example, the gel is placed on Kodak X-OMAT AR film, matching up the film with one of the corners of the gel to allow subsequent superimposition for excising bands for counting. The film is exposed for 20–100 min at 22° C. (no screen) or 30 min –4 h with intensifying screen at –80° C., with the actual time depending on the amount of the radioactive label.

For quantitation, the radioactive bands is excised and radioactivity determined by scintillation counting. The exposed film is taped to a light-box and the gel placed over the film and taped in place. The position of dyes aids alignment. The substrate and product bands are excised and placed in 4 ml of scintillation fluid (e.g. Ecolume, ICN Biomedicals, Radiochemical Division. Irvine. Calif., U.S.) in a mini-vial and counted for 2 minutes or until 40,000 counts have been recorded in the $^{32}$p channel of a scintillation counter.

The assay provides a sensitive, reliable, and rapid manner of detecting class II AP endonuclease activity.

Example 21

Transduction of nfo::kan mutation from *E. coli* BW528 into *E. coli* MM294

*E. coli* BW528 cells (Cunningham, et. al. *J. Bacteriol.* 168:1120–1127 (1986) were grown overnight (about 16 hours) in LB broth at 37°. Fifty microliters (50 µl) was subcultured into 5 ml LB containing 0.2% w/v glucose and 5 mM calcium chloride. The cultures were incubated for 30 min at 37° with aeration, and 0.1 ml bacteriophage P1 vir was added to give ca. $5\times10^8$ phage/ml. The cells were then shaken 3 h for phage development and cell lysis. Chloroform (0.1 ml) was added and the culture vortexed. The cell debris was pelleted by centrifugation at 4500 X g for 10 min, and the supernatants were transferred to fresh sterile tubes containing 0.1 ml chloroform. After mixing, the phage preparations were stored at 4°.

Titre (number of viable phage/ml) of the phage preparations was determined as follows: the phage preparations were serially diluted $10^3$, $10^5$, and $10^6$ fold in 10 mM magnesium sulfate and 5 mM calcium chloride and 5 btl of each dilution spread as a patch of approximately 1 cm diameter on a lawn of *E. coli* MM294 (Meselson, et al., Nature 271:1110–1114 (1968))cells in TB top agar on a LA plate (LB solidified with 1.5 % agar). The lawn was made by adding 0.1 ml suspension of *E. coli* MM294 cells in 10 mM magnesium sulfate, 5 mM calcium chloride (approximately. $10^9$/ml) to 3 ml molten TB top agar cooled to 45°. The mixture was then poured onto the surface of a LB plate. The plates were incubated at 37° overnight and the number of plaques counted at a suitable dilution to calculate the titre. The resulting preparation of P1 vir had a titre of $4\times10^8$ plaque forming units/ml.

A 5 ml LB culture of *E. coli* MM294 was grown overnight, and the cells collected by centrifugation at 1500 xg for 10 min. The cells were resuspended in 2.5 ml 10 mM magnesium sulfate and 5 mM calcium chloride. Aliquots (0.1 ml) of the cells were placed in test tubes with 0.01, 0.05, 0.1 ml P1 vir lysate described above, and incubated 30 min at 30° for infection. Sodium citrate (0.1 ml of I M solution) and 1 ml LB were added. Cells were grown 1 h at 37° to express the drug resistance before 2.5 ml molten (45°) LB top agar (LB with 0.7% agar) was added, and the mixture plated on LA plates containing 25 mg/l kanamycin sulfate (LA $Km_{25}$). The plates were incubated at 37° for 2 days.

Two kanamycin resistant colonies were obtained from the tube with 0.01 ml phage. These colonies were streaked out on LA $Km_{25}$ plates and a single colony tested for loss of class II AP endonuclease activity by assay with an abasic substrate. No cutting of the abasic substrate was observed, confirming the loss of class II AP endonuclease. This strain was named *E. coli* MM294 nfo::kan.

Example 22

Subcloning of the Gene from *Thermus thermophilus*

Step A: Isolation of plasmid pCS10 from *T. thermophilus*

The clone bank of *T. thermophilus* of Lauer, et al., *J. Bacteriol.* 173: 5047–5053 was used. It had been constructed in *E. coli* strain HB101 by cloning 7- to 30-kb DNA fragments generated by partial Sau3AI digestion of *T. thermophilus* chromosomal DNA into pTR264 digested with BclI and treated with calf intestinal phosphatase.

Plasmid DNA of the *Thermus thermophilus* clone bank consisting of 4 pools of ~400 clones per pool with an average insert size of 10 kb of chromosomal DNA, (DNA concentration ca. 0.5 mg/ml) was diluted 10 fold with $T_5E_{0.5}$, and added to the competent *E. coli* MM294 nfo::kan cells prepared as described in Example 1. After 30 min on ice, the tubes were heat shocked for 90 sec at 42° C. followed by cooling on ice for about 1 min. One ml of SOC medium was added, and the cells shaken for 1 h at 37° for expression of the tetracycline resistance gene on the plasmid. A 50 µl aliquot was plated onto LA tetracycline (5 µg/ml) and the remainder spun down and plated on a single plate. The plates were incubated at 37° overnight.

The dilute plates contained roughly 200 colonies, and the concentrated plate contained over 1000 colonies in the case of all four pools. The colonies on the concentrated plate were scraped up in 3 ml LB, and another 1 ml LB used to wash the surface of the plate. The final recovered volume was approx 3 ml. One ml of the resuspended cells was used to inoculate 250 ml LB Tc5 and cultures grown at 37° for about 3 h. Cells were collected by centrifugation, resuspended in crushing buffer (50 mM Tris/HCl pH 7.4, 10 mM $MgSO_4$, 180 µM $CoCl_2$, 5% v/v glycerol), and respun. Cells were finally resuspended in 6 ml crushing buffer and cells broken at 14,000–16, 000 psi in a French Press. Cell debris was removed by centrifugation at 15,000 rpm (26,900 xg) for 15 min. A 200 µl aliquot of the cleared supernatant was made 50 mM in NaCl, and heat treated at 90° for 5 min, followed by cooling on ice for 1 min. Precipitated protein was removed by centrifugation in a microfuge at room temp for 5 min. A 10 µl aliquot was then assayed for class II AP endonuclease activity against both hairpin substrates #1, and #2. Assays were done with and without the addition of herring sperm DNA with 3' labelled hairpin and 5xLCR buffer.

A 10 µl sample was removed after 1 h into an equal volume of 98% formamide-dye mix and the remainder stopped after 17 h as above. A 15 µl sample of the stopped assays was run on a 20% polyacrylamide/urea/TBE gel (45 min, 800 V), and exposed to film for 100 min. Class II AP endonuclease activity was obtained from Pool #1 and #3 on hairpin 2. Pool #1 was chosen for further work.

A second transformation of the DNA of the *Thermus thermophilus* clone bank, prepared above, was performed with competent *E. coli* MM294 nfo::kan cells. Eleven plates (labelled A–K) of 50 patches each were made, in duplicate, by patching out colonies from the transformation onto LA $Tc_5$. Horizontal rows of each plate (6–10 patches) were scraped into 500 µl 0.85% saline, 10% glycerol, and resuspended. A 125 µl aliquot of each of the pools from a single plate were inoculated into a single 250 ml LB $Tc_5$ culture, such that each culture represented a single plate of 50 patches. These cultures were grown 16.5 h at 37° with shaking and harvested by centrifugation (5 min, 5000 rpm, 6×250 ml rotor). The cell pellets were washed in 20 ml 0.85% saline, 50 µM $CoCl_2$, and resuspended in 6 ml crushing buffer. Cells were crushed, spun, heat-treated and assayed for 1 h as described above. Plates A, B, and I showed a product band indicative of class II AP endonuclease activity. Plate I was chosen for further investigation.

Pools of 6–10 patches from plate I of clone bank were screened in the following manner. Six 250 ml LB $Tc_5$ cultures were set up and inoculated with pools of 6–10 clones from plate I as for experiment with pools of 50. Cultures were grown and extracts made, heat treated and assayed as for previous experiment with pools of 50. A 30 min time sample (10 μl) was removed from the assay and electrophoresed on polyacrylamide as before. Class II AP endonuclease -like activity was observed in the culture corresponding to ten patches from rows 1 and 2 of plate I.

Further analysis of these 10 clones indicated that patch #9 was responsible for the class II AP endonuclease activity. Patch #9 was streaked out for single colonies, and two singles retested for class II AP endonuclease activity. Both were positive for cutting of the abasic hairpin #2 in a 30 min assay. One was chosen for storage. The plasmid was called pCS10, and the strain *E. coli* MM294 nfo::kan (pCS10).

DNA of pCS10 was purified by alkaline lysis, followed by cesium chloride gradient centrifugation from a 250 ml LB Tc$_5$ culture using standard procedures known to those skilled in the art such as is found in Maniatis, supra. The DNA preparation had a concentration of 420 μg/ml.

Step B: Sau3AI digest of pCS10 to prepare pCS11

Plasmid vector pIC20H was cut with Bam HI and dephosphorylated with bacterial alkaline phosphatase (BAP). pIC20H has a polylinker in the a fragment of β galactosidase such that inserts into the polylinker cause loss of the β galactosidase activity and loss of color formation on β galactosidase indicator plates. This allows the identification of inserts in the vector. Digestion was done at 37° for 90 min, followed by phenol extraction and ethanol precipitation. The plasmid DNA was resuspended in 20 μl T$_5$E$_{0.5}$, and 15 μl treated with the phosphatase according to manufacturers instructions. The reaction was incubated 1 h at 65°. 30 μl of H$_2$O and 1 μl 0.25 μl EDTA were added and the reaction heated 10 min at 50°. The digest was phenol-extracted and ethanol-precipitated. The plasmid DNA pellet was resuspended in 10 μl T$_5$E$_{0.5}$.

Next, plasmid pCS10 was partially digested with Sau3AI 37° for 20 minutes and stopped by heating 10 minutes at 68°. A μl aliquot was run on an agarose gel to determine degree of cutting. Digestions 3, 4, and 5 were not significantly digested, so they were redigested by addition of 2 μl 1:20 Sau3AI to each tube for 20 min followed by heat inactivation at 65° for 10 min. The whole digest was run on a 1% agarose gel in TAE. After staining, agarose slices were cut out under long wave uv, corresponding to 1–1.5 kb, 1.5–2 kb, 2–3 kb and 3–4 kb. The DNA was isolated using the Gene-clean kit (BIO-101, La Jolla, Calif.) and resuspended in approximately 15 μl T$_5$E$_{0.5}$. These fractions were then ligated to plasmid pIC20H prepared above. (Marsh, et al, *Gene* 32, 481–485, 1984).

Ligations (10 μl) were set up containing 0.3 μg pIC20H (1 μl) and 2 μl of one of the size fractions isolated from agarose. After overnight ligation at 16°, 1 μl of the ligations was transformed into 50 μl DH5aF' according to manufacturers instructions, except that the cells were grown out for 1 h in 2 ml SOC before spreading onto LA Amp$_{100}$ X-Gal plates. For the 1–1.5 kb size range, approximately 205 white and 7 blue colonies appeared in total. A second transformation was done with the ligation of 1–1.5 kb fragments for more transformants. Plasmid DNA minipreparations were done on 10 transformants. HindIII digestions showed that the insertion was in the selected size range in all cases.

Eight plates of 50 colonies each of the 1–1.5 kb size range (total=400 colonies) were patched out on LA Amp$_{100}$ X-Gal in duplicate. Plates were incubated overnight at 37°. Groups of 10 patches from one of the duplicate plates was scraped up and resuspended in 0.5 ml 0.85% saline, 10% glycerol. 0.25 ml of each of the five pools from the same plate were inoculated into LB Ampre$_{100}$, and grown for 4 h at 37°. Cells were harvested and extracts made and assayed as for the previous screening of the clone bank. Assays were stopped at 40 min and samples electrophoresed as before. Plates #1 and #2 both showed activity. Subpools of 10 colonies from both these plates were grown and extracts tested for class II AP endonuclease activity. Pool D (#Patches 31–40) from plate #1 and pool B (#Patches 11–20) from plate #2 were identified as giving activity. These colonies were individually tested and #36 (plate #1) and patch #20 (plate #2) were identified. These were purified through single colonies on LA Amp$_{100}$, and DNA preps made by CsCl-gradient centrifugation Restriction mapping indicated identical 1.4 kb inserts in the two plasmids The plasmid from plate# 1, patch #36 was named pCS11.

The 1.4 kb insert in pCS11 was restriction mapped with Bam HI, BglII, PstI, SacI, SmaI, SalI, XbaI and XhoI. The insert contained sites for BglII, SacI and XhoI, but no sites for the other enzymes. The sites for BglII, SacI and XhoI were roughly equally spaced 0.3–0.4 kb apart and this was exploited for subcloning into M13 for sequencing.

Step C: Subcloning of pCS11 into M13mp18 for Sequencing

Four micrograms of pCS11 was digested with 10–15 units of the appropriate restriction enzyme in a 20 μl reaction using the recommended buffer at 37° for 2.5 h. Digests were stopped with 2 μl gel loading buffer, and 10 μl electrophoresed on a 1.2% agarose gel in TAE. Bands corresponding to the desired fragment (see Table below) were excised and the DNA isolated using the Prep-a-Gene Kit (BioRad). The DNA was resuspended in 15 μl T$_5$E$_{0.5}$. Ligations were set up with 13 μl DNA fragment (approx. 0.15 μg) and 0.1 μg M13 cut as shown in table below. The M13 (0.5 μg) was cut with the appropriate enzymes at 37° for 1.5 h, phenol extracted and ethanol precipitated, and the pellet resuspended in 10 μl T$_5$E$_{0.5}$. It was then 5' dephosphorylated with bacterial alkaline phosphatase (30 Units) in a 15 μl reaction for 1 h at 65°. Phosphatase was removed by phenol extraction and the DNA recovered by ethanol precipitation as above. The DNA was resuspended in 10 μl T$_5$E$_{0.5}$.)

| Fragment of pCS11 | Size | M13 derivatives used | M13 digested with: |
| --- | --- | --- | --- |
| PstI - Asp718 | 1.5 kb | M13mp18 & M13mp19 | PstI/Asp718 |
| HindIII - BglII | 0.4 kb | M13mp18 & M13mp19 | HindIII/Bam HI |
| BglII - SacI | 0.4 kb | M13mp18 & M13mp19 | Bam HI/SacI |
| SacI - SmaI | 0.65 kb | M13mp18 & M13mp19 | SacI/SmaI |
| SacI - Xho I** | 0.35 kb | M13mp18 & M13mp19 | SacI/SalI |

Sequencing of M13 clones was done using the method of Sanger et. al., 1977. *Nat. Acad. Sci.* USA 74:5463–5467, employing M13 templates prepared as described by Messing, 1983. *Methods in Enzymol.* 101:20–78. Sequencing of double stranded templates was performed as described by Zhang et al., 1988. *Nucleic Acids Res.* 16:1220.

The DNA sequence of the inset in pCS11 was 1469 base pairs. Translation of the sequence in all reading frames was done. A single reading frame of 813 base pairs (including TAA stop codon) encoding a 270 amino acid polypeptide was deduced from the sequence. The ATG start codon was preceded by a weak Shine-Dalgarno (ribosome binding) site for *E. coli*. The protein had a predicted mol. wt. of 29,088 and a predicted isoelectric point of 6.17. The G-C content of the coding region was 71.1%. A series of 10 synthetic DNA sequencing primers, spaced roughly 200–250 base pairs apart, were designed and used to re-sequence the coding region. This sequence is shown in FIG. 1A of WO93/20191 which corresponds to U.S. Ser. No. 07/860,861 and 07/869,306.

Example 23

Insertion of a Ribosome Binding Sequence 5' to the *T. thermophilus* Class II AP endonuclease Coding Sequence for Efficient Expression in *E. coli*

The polymerase chain reaction (PCR) was used to insert a ribosome binding sequence (i.e., Shine-Dalgarno sequence) particularly effective in *E. coli* at the 5'-end of the class II AP endonuclease gene. The PCR product was about 151 base pairs, and contained about 122 nucleotides of the 5'-end of the coding sequence. The intact class II AP endonuclease gene was then reassembled in vitro prior to overexpression in a suitable vector.

A 46-mer oligonucleotide PCR primer having the sequence GGCTAGCCCGGGATCCAGGAGGTATAAAA ATGCCGCGCTACGGGTT 3' (SEQ ID No. 41) (ribosome binding sequence and start codon are underlined) contained in order from the 5' end: NheI, SmaI and BamHI restriction sites followed by a Shine-Dalgarno sequence (AGGAGGT) placed six base pairs from the ATG start codon and followed by seventeen nucleotides homologous to the *T. thermophilus* class II AP endonuclease gene. An internal leftward reading sequencing primer having the sequence 5' -CAGCTC-CGCGGGGCTTTT-3 ' (SEQ ID No. 42) was used as the other PCR primer. PCR was done using standard methodology (McConlogue, et al., *Nucleic Acids Res.*, 16:9869 (1988)) except that a mixture of 7-deaza-dGTP and dGTP (in a 3:1 ratio) was used. A gel-purified fragment of plasmid pCS11 (8 ng) which had been restricted with HaeII and XmaIII was used as the target for PCR. This resulted in a fragment of about 150 bases which included the restriction sites and the ribosome binding sites (the Shine-Dalgarno sequence). This PCR product was reamplified by a second round of PCR and then treated with mung bean nuclease (to give DNA blunt ends) for 35 min at 30°, extracted with phenol, and precipitated with ethanol. The DNA was resuspended in 10 µl H$_2$O, heated 5 min at 60° to inactivate the nuclease, and 4 µl used for ligation.

The product was then ligated into pUC19 (see Yanisch-Perron et al., 1985, supra; Roberts,1986, supra) and transformed into competent *E. coli* DH5aF cells according to manufacturers instructions up to the heat shock step. Cells were then grown in SOC medium for 1 h at 37° prior to plating on LA Amp$_{100}$ X-Gal IPTG plates. After overnight incubation, 3 white and 1 light blue colony were obtained together with 76 blue (non-recombinant) colonies.

DNA plasmid minipreparations were done and the results showed the expected size in two of the clones, designated PCR#2 and PCR #4. DNA sequence analysis demonstrated that the clones contained the ribosome binding site upstream of the ATG start codon.

Example 24

Reassembly of the Intact *T. thermophilus* gene and Construction of Plasmid pTT1

Plasmid pCS11 (2.5 mg) was restricted with BglII and HindIII and the digests electrophoresed on agarose. An approximately 1.1 kb fragment was isolated and the DNA recovered using the Prep-a-Gene kit (BioRad) in a final volume of 15 µl. A 6 µl aliquot of this was ligated into PCR#2 and PCR#4 which had been restricted with BglII and HindIII and dephosphorylated with phosphatase. The ligations were transformed into DH5a cells; plasmid DNA minipreparations were made for ten of the transformants from each cloning and the DNA cut with BamHI and HindIII. One ligation product into pPCR#4 contained the correct 1.1 kb insertion and was designated pPCR#4-8. This construct was then digested with BamHI and HindIII. An approximate 1.3 kb band was isolated and ligated into plasmid pGL516x (pGL516 of Lauer, et al., supra, modified by addition of XhoI linker at Bst X site in the lambda promoter) which had been restricted with BamHI and HindIII and dephosphorylated.

The ligation was electroporated into *E. coli* CS1 and the transformants selected for ampicillin resistance. Resultant clones were tested for the insert. Some transformants seemed to have a double insertion. Candidates were grown and extracts from the clones tested for class II AP endonuclease activity. A clone, pTT1, identified as an overproducer, contained an insertion of the intact class II AP endonuclease gene followed downstream by a tandem copy of a portion of the gene from the BglII site to the 3' end, similar to the tandem insertion in pPCR#4-8.

Example 25

Reassembly of the Intact *T. thermophilus* gene and Construction of Overexpressing Plasmids pTT2, pTT3, pTT4, and pTT5

Plasmid pCS11 was restricted with Bgl II and a 1.1 kb fragment isolated. This fragment was then ligated to pPCR#2 and pPCR#4 which had been cut with Bgl II to yield plasmids pPM2010 and pPM2020, respectively which now contain the reassembled intact class II AP endonuclease gene.

The class II AP endonuclease fragments in pPM2010 and pPM2020 were excised with BamHI and isolated from an agarose gel. Plasmid DNA minipreparation was used for isolation of the approximately 1 kb fragment.

pGL516 (1.5 µg) and pGL516X (1.4 µg) were cut with BamHI, dephosphorylated, and phenol extracted/ethanol precipitated. The DNA was resuspended in a final volume of 15 µl, and 1.2 µl used in each ligation.

The 1 kb fragments from pPM2010 and pPM2020 were ligated into both pGL516 and pGL516X (a total of 4 ligations). A 2 µl aliquot was electroporated into CS1 electrocompetent cells. Cells were made electrocompetent according to a procedure published by BioRad and provided with their electroporation device. The only modification was that the cells were grown at 30° rather than 37°. After electroporation and outgrowth in SOC medium, the cells were plated on LA Amp$_{100}$.

Transformants were patched onto LA Amp$_{100}$ and also grown in 2 ml LA Amp$_{100}$ for DNA minipreparation. The miniprep DNA was double digested with BglII and EcoRI, and run on an agarose gel. The enzymes cut in the class II AP endonuclease gene and in the vector at the promoter-distal end of the insert to give a 1050 base pair insert piece joined to an approximately 375 base pair vector fragment yielding a diagnostic fragment of approx. 1425 bp. Several correct candidates were present for each of the four ligations.

One candidate from each cloning was selected and named as follows:

pTT2: reassembled class II AP endonuclease from pPM2010 in pGL516 pTT3: reassembled class II AP endonuclease from pPM2020 in pGL516 pTT4: reassembled class II AP endonuclease from pPM2010 in pGL516X pTT5: reassembled class II AP endonuclease from pPM2020 in pGL516X.

Example 26

Construction of Plasmids pTT7, pTT8, pTT9, and pTT10

The class II AP endonuclease gene in pTT3 and pTT5 was partially digested with BamHI and samples removed at 5, 10, 15, and 20 min into loading buffer. Samples were electrophoresed in an agarose gel and the approx. 6.7 kb singly cut product excised. The DNA was isolated with the Prep-a Gene (BioRad) kit, and digested with NheI for 10 min at 37°. Deoxynucleotide triphosphates were added to about 32 μM and Klenow fragment was added to fill in the overhangs. After 10 min at 30°, the reaction was stopped with loading buffer, and the DNA run on a 0.7% agarose gel. The upper band corresponding to DNA cut at the promoter proximal BamHI site and NheI, was excised and the DNA isolated from the gel slice as above.

The DNA was then self-ligated to reseal the blunted ends, and electroporated into CS1 as for construction of pTT3 above. Eight minipreps of each cloning were made, double digested with BamHi +SalI, and electrophoresed on a 0.8% agarose gel.

Two different plasmid derivatives resulted from this experiment. pTT7 and pTT8 (from pTT3 and pTT5, respectively) both contained a filled-in promoter-proximal BamHI site as the only modification. pTT9 and pTT10 (from pTT3 and pTT5, respectively) contained a deletion of approximately 180 base pairs between the promoter proximal BamHI and NheI sites.

The relative activity of the various class II AP endonuclease producing plasmids was tested in a semiquantitative assay with hairpin #2. The class II AP endonuclease activity of extracts of CS1 (pTT1) was more than 300 times higher than extracts of *E. coli* nfo:kan (pCS11). The relative activities of the pTT series of overproducing plasmids was as follows:

| pTT1: | pTT3: | pTT7: | pTT9: | pTT10: |
|---|---|---|---|---|
| 1: | 1.8: | 6.8: | 2.4: | 1.6 |

Example 27

Purification of Recombinant *T. thermophilus* Class II AP endonuclease from *E. coli* CS1 (pTT7)

Cell paste (70.6 g) of *E. coli* CS1 (pTT7) was thawed and resuspended in 211.8 ml (3 vol.) Buffer A (25 mM Tris/HCl pH 7.4, 1 mM MgSO$_4$, 50 μM CoCl$_2$, 5% glycerol) containing 0.1 M NaCl at room temperature (22° C.). Cells were broken at 14,000 psi in a French Press in 45 ml aliquots and the resulting extract centrifuged at 14,000 rpm (23,420 ×g) for 20 min to remove cell debris. The supernatant was incubated at 37 ° C. for 1 h during which time precipitation of some contaminating proteins occurred. After centrifugation as above, the extract was cooled 2 hours on ice, recentrifuged as above, and the supernatant filtered through a 5 mm filter. This yielded 196 ml of extract, which was stored at −80° C.

The filtered extract (196 ml) was thawed, diluted to 500 ml with buffer A, and centrifuged at 14,000 rpm for 30 min to remove precipitated protein. A 100 ml aliquot was loaded onto a 100 ml Blue Sephrose (Pharmacia) radial flow column equilibrated in Buffer A at room temperature at a flow rate of about 5 ml/min. (The remainder was frozen as 100 ml aliquots at −80° C.). The column was then washed with Buffer A until the OD returned to nearly baseline. A 500 ml gradient was run from 0–1.0 KCl at 5 ml/min. Twenty eight 20 ml fractions were collected. Class II AP endonuclease eluted mainly in fractions #8–26 which were pooled and stored at −80° C.

The other four 100 ml aliquots of the diluted crude extract were similarly chromatographed on Blue Sepharose, and fractions #8–26 pooled. The pools from the 5 columns were then pooled and concentrated by ultrafiltration (YM1 membrane, Amincon) to about 120 ml and dialysed overnight against 4L Buffer A at 4° C. The pool was then centrifuged at 12,000 rpm (17,210 ×g) for 20 min to remove precipitated protein and column material, and filtered through a 1.2 micron filter.

The pool was then divided into three 40 ml portions and one portion was loaded onto a 50 ml Heparin agarose (Sigma) radial flow column prepared in Buffer A at approx. 1.5 ml/min. After washing unbound protein from the column, 150 ml gradient was run from 0.0–1 M KCl at 1.5 ml/min. Fractions (3.75 ml) were collected. A major peak of uv-absorbing material with a shoulder was observed. Fractions 15–54 contained class II AP endonuclease activity, and these were pooled. The other two aliquots were similarly processed except that Heparin Sepharose CL-6B was used with similar results. Fractions 18–48 contained class II AP endonuclease activity, and these were pooled.

The pooled fractions (about 266 ml) were concentrated by ultrafiltration (YM1 membrane, Amincon) to approx. 50 ml and then heat-treated at 75° C. in a 50 ml polypropylene tube, by placing in a boiling water bath, with constant stirring. The temperature was monitored, and the tube removed to ice when the temperature reached 75° C. (6.5 min). After 4 h on ice, the preparation was centrifuged to remove precipitated protein as before, and the supernatant filtered through a 0.8 μm filter. The pool was then further concentrated to 4.3 ml by ultrafiltration (YM5 membrane, Amincon) and filtered through a 0.8 μm filter.

230 μl samples were subjected to HPLC size exclusion chromatography on a TSK-G30008W column (7.5 mm dia. ×250 mm, BioRad) in 50 mM MES, 200 mM NaCl pH 6.8 at 1 ml/min. One-ml fractions were collected. Activity was found in the major 280 nm-absorbing peak (frac. 13–20).

A total of 19 such runs were done, and the class II AP endonuclease fractions pooled. The pool (about 140 ml) was then concentrated to 14.5 ml by ultrafiltration (YM5 membrane, Amincon). The final yield of class II AP endonuclease was 14.5 ml at 4.45 mg/ml. The enzyme was analyzed for purity by SDS-polyacrylamide gel electrophoresis. After staining with Coomassie Blue, a major band was visible at about. 29,000 daltons, corresponding to the molecular weight predicted for endonuclease IV from the DNA sequence (29,088). The purity was approximately 95%.

Example 28

Growth of E. coli CS1(pTT7) for Overproduction of Cloned Thermostable Class II AP endonuclease The same medium was used throughout, and was composed of a 1:1 mixture of "2 × seed medium" and LB, and included 100 mg per liter ampicillin. The "2 × seed medium" contained (per liter): 20 g glucose, 2 mM $MgSO_4$, 0.2 mM $CaCl_2$, 2 ml micronutrients, 44 mM $KH_2PO_4$, 138 mM $K_2HPO_4$, 3.4 mM NaCl, 76 mM $(NH_4)_2SO_4$, 0.001% vitamin B1, 20 ml Fe citrate solution. [Micronutrient solution contained per liter: 0.15 g $Na_2MO_4.2H_2O$, 2.5 g $H_3B0_3$, 0.7 g $CoCl_2.6H_2O$, 0.25 g $CuSO_4.5H_2O$, 1.6 g $MnCl_2$, and 0.3 g $ZnSO_4.7H_2O$. Fe citrate solution contained per liter: 0.2 g $FeSO_4.7H_2O$, 100 g $Na_3$ $Citrate.2H_2O$.]

A 1 ml frozen stock of CS1 (pTT7) (a stationary phase LB culture that had been made 5% in glycerol and frozen at −80° C.) was thawed and added to 25 ml fermentation medium. The culture was grown 12h at 30° C., then a 4 ml aliquot added to 950 ml of the same medium and grown 12h at 30° C. This was then added to 10 L of medium in a Chemap CF 2000 fermentor and grown for 7h at 30° C. (optical density at 600 nm approx. 9.5) During growth in the fermentor, the pH was monitored constantly and automatically adjusted to 7 with $H_2SO_4$ or $NH_3$. The culture was also stirred rapidly and bubbled vigorously with air. After 7h at 30° C., the temperature was raised to 42° C. for 2h to induce production of the class II AP endonuclease, during which the optical density did not change appreciably. The culture was then placed in a container on ice and the cells collected by centrifugation at 8,000 rpm (10,800 ×g) for 15 min in 500 ml bottles. The bottles were filled and spun several times to give an accumulated cell pellet of roughly 70 g per bottle. The total yield was 285 g wet weight. The cell paste was frozen in the centrifuge bottles at − 80° C.

Example 29

Identification of Class II AP endonuclease from T. thermophilus

T. thermophilus HB8 ATCC. 27634 was grown and an extract tested for class II AP endonuclease activity using hairpin #1 (defined, supra) as substrate in an assay buffer consisting of 25 mM EPPS, pH 7.6, 50 mM NaCl, 1 mM DTT, 1 mM EDTA and 50 mg/mL bovine serum albumin. The extract gave several bands from hairpin #1. However, none corresponded to that expected of class II AP endonuclease activity. It appeared that there was rapid destruction of the substrate by nuclease activity to give the observed bands, despite the presence of EDTA. Crude extracts showed no definitive class II AP endonuclease but results indicated the presence of an EDTA-resistant nuclease activity, herein defined as endonuclease X.

Therefore, in order to separate the class II AP endonuclease from endonuclease X, the crude extracts were treated with protamine sulfate to precipitate the DNA, followed by chromatography over a size exclusion column (Ultrogel Ac54, 13 cm×1 cm dia.) at 0.5 ml/min at room temperature (about 22° C.). Forty 0.2 ml fractions collected and the fractions were assayed with hairpin #1 as substrate. The endonuclease X activity was recovered in fractions 12–28. In the assay only a single band of about 13 nucleotides was obtained from the abasic hairpin #1 rather than the seven nucleotide fragment expected from the class II AP endonuclease activity. This result differed from the crude extract in that the crude extract gave multiple bands, but still no class II AP endonuclease activity was evident in any of the fractions.

Subsequentially, T. thermophilus extract (70 ml which had been treated with protamine sulfate to precipitate DNA which tends to interfere with the chromatography stationary phase) was chromatographed on a DEAE Sepharose Fast Flow column (7 cm×4.4 cm dia.) equilibrated with 50 mM Tris/HCl pH 7.4, 1 mM DTT, 5% v/v glycerol, 25 mM benzamidine Cl using a 800 ml gradient from 0–1 M KCl at 4° C. A total of 32×12 ml fractions followed by 8×28 ml fractions were collected. No class II AP endonuclease activity was evident in any of the fractions. Endonuclease X activity eluted immediately after the flowthrough fraction. The endonuclease X fractions (# 11–17, 84 ml) were pooled, concentrated to 3 ml and chromatographed on a size exclusion column (Sephacryl S100HR, 55 cm×2.2 cm dia.) in order to test the possibility that there was class II AP endonuclease in this strain but that it had co-eluted with the endonuclease X.

Fractions off the column were assayed. High endonuclease X was recovered in fractions 23 through 41. In addition, fractions 41–47 showed a band that corresponded to one expected from an class II AP endonuclease activity.

In conclusion, class II AP endonuclease activity was identified in T. thermophilus after two purification steps which separated class II AP endonuclease activity from the endonuclease X activity.

Example 30

Demonstration of Class II AP endonuclease Activity in Thermophiles Sulfolobus solfataricus and Thermus aquaticus Three Thermus strains, T. flavus (ATCC. 33923), T. sp (ATCC. 31674), T. aquaticus (ATCC. 25104) and the archebacterium Sulfolobus solfataricus (ATCC. 35091) were obtained from the American Type Culture Collection (ATCC) and grown using standard culture media recommended by the ATCC, and extracts tested with hairpin #1 as defined in Example 9.

Class II AP endonuclease was clearly seen in the *T. aquaticus* and in the *S. solfataricus* crude extracts. However, its activity was masked by the presence of endonuclease X in *T. flavus* and *T. sp.*

Example 31

Purification of Native Class II AP endonuclease from *T. aquaticus*

*T. aquaticus* ATCC. 25104 frozen cell paste (38 g) was thawed, washed in 100 ml saline (0.85 %w/v NaCl), centrifuged, and resuspended in 2 volumes buffer (80 ml; 50 mM Tris/HCl pH 7.4, 5 % glycerol, 0.5 mM DTT). The cells were broken and debris removed by centrifugation. The supernatant (93 ml) was made 0.4 % w/v in Polymin P/HCl pH 7.9 (3.9 ml of 10% w/v stock) with stirring on ice. Comparison of the activity of the supernatant before and after Polymin P treatment indicated that significant activity was lost.

An aliquot (20 ml) of the extract was diluted with 50 ml buffer (20 mM potassium phosphate pH 7.0, 1 mM DTT, 10% v/v glycerol) and loaded onto a Blue sepharose column at 4° C., and washed with 15 ml buffer. Over 90% of the protein did not bind to the column as judged by the optical density of the material that did not bind. A 2×150 ml gradient of 0.1–1.0 M NaCl was then used to develop the column. Fractions (80 drops, about 4 ml, 74 fractions total) were collected, and 2 μl aliquots assayed to locate the endonuclease IV peak. Endonuclease IV eluted broadly between fractions # 4–48. Fractions. #16–40, (roughly 0.3–0.6 M NaCl) contained most of the activity. Significant activity was also present in the flowthrough fraction, indicating that all of the class II AP endonuclease like activity did not bind. Fractions were made roughly 33% in glycerol and frozen at −20° C.

Pools of fractions # 14–19, 20–25, 26–31, and 32–37 were used to demonstrate that this activity yielded ligatable ends with abasic substrate and a target. Pools of 26–31, and 32–37 were concentrated roughly 3-fold and used for heat stability studies resulting in the discovery of the need for a divalent metal for stability.

Example 32

Heat Stability of Partially Purified Cloned *T. thermophilus* Class II AP endonuclease Cloned *T. thermophilus* class II AP endonuclease from the chromosomal clone [MM294 nfo::kan (pCS10)] was partially purified on a Blue Sepharose column. Two class II AP endonuclease -containing fractions were eluted in 1 M NaCl and concentrated and used to demonstrate heat stability. Heat cycling (20 μl) was done in LCR buffer. Fifty cycles were done of heating to 90° (max. rate), holding for 30 sec; cooling to 50° (max. rate); and holding at 50° for 45 sec. An aliquot of the reaction was then diluted 10-fold and assayed in a modified assay buffer containing 50 mM EPPS/KOH pH 7.6, 80 mM KCl, 1 mM $MgCl_2$, 10 mg/l gelatin, 0.1 mM $CoCl_2$ for 10 min at 50°. In all cases, the degree of cutting of the substrate was essentially equal to or greater than the activity of the control kept on ice, thus demonstrating the *T. thermophilus* preparation was substantially stable to heat cycling.

What is claimed is:

1. In a ligase chain reaction method for amplifying a target nucleic acid sequence, said method including: (a) providing at least two sets of two probes, the 3' end of an upstream probe being ligated to the 5' end of a downstream probe in the presence of target to form a primary ligation product and the second set of probes hybridizing to the primary ligation product and being ligated to each other to form a secondary ligation product; (b) repeatedly denaturing the hybridized strands, reannealing additional probes and ligating them; and (c) detecting to what extent ligation products have formed, the improvement comprising:

(a) providing in at least one of the upstream probes a 3' end modification such that the probe is incapable of ligation to its downstream partner, said 3' end modification being correctable substantially only when the modified probe is hybridized to the target sequence;

(b) hybridizing the modified probe to the target, if present, to form a modified probe-template complex;

(c) correcting the modification in a target dependent manner using endonuclease IV activity to create a 3' hydroxyl end, thus allowing the corrected probe to be ligated to its downstream partner;

(d) ligating the corrected probe to its downstream partner to form an amplification product; and (e) dissociating the amplification product from the target and repeating the hybridization, correction and ligating steps to amplify the desired target sequence.

2. The method of claim 1 wherein said 3' modification comprises a blocking moiety attached to said probe such that it blocks a chemical group required in the ligation step.

3. The method of claim 2 wherein the blocking moiety is of the form:

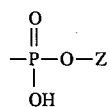

wherein Z is selected from the group consisting of —H; —(CH$_2$)$_n$ CHO, where n is from 1 to about 3; -deoxyribose; and -dideoxyribose.

4. The method of claim 3 wherein said blocking moiety is phosphate.

5. The method of claim 1, wherein at least said correcting step is performed in the presence of available divalent cation selected from cobalt and manganese at a concentration of at least about 0.05 mM.

6. The method of claim 5, wherein said divalent cation is at a concentration from about 0.1 to about 2.0 mM.

7. The method of claim 5, wherein said divalent ion is cobalt at a concentration of about 0.5 mM to about 1.0 mM.

8. The method of claim 5, wherein said divalent ion is manganese at a concentration of about 0.5 mM to about 1.0 mM.

9. The method of claim 1, wherein one or more of the steps is performed in the presence of divalent magnesium ion at a concentration of about 0.5 mM to about 20 mM.

10. The method of claim 1, wherein said two sets of two probes are oligodeoxyribonucleotide probes, except that at least one of said probes includes at least one ribonucleotide residue.

11. The method of claim 10, wherein said at least one ribonucleotide residue occurs immediately 5' to the 3' modification.

12. The method of claim 3, wherein said probe having the 3' end blocking moiety further includes at least one ribonucleotide residue, and the blocking moiety is attached to the 3' position of said ribonucleotide.

13. The method of claim 10, further comprising, after the detection step, a step of cleaving ligation products using RNase or alkali.

14. The method of claim 10, further comprising, prior to amplification, a step of cleaving ligation products using RNase.

15. The method of claim 14, wherein the blocking moiety is of the form:

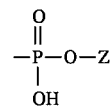

wherein Z is selected from the group consisting of —H; —(CH$_2$)$_n$ CHO, where n is from 1 to about 3; -deoxyribose; and -dideoxyribose.

16. The method of claim 2 wherein said blocking moiety is a nucleic acid overhang containing an abasic residue immediately 3' to the point of intended ligation.

17. The method of claim 16 wherein said correction of the modification comprises cleavage of said modified probe on the 5' side of said abasic site, substantially only when said modified probe is hybridized to target or to ligation product.

18. The method of claim 16, wherein at least said correcting step is performed in the presence of available divalent cation selected from cobalt and manganese at a concentration of about 0.05 mM to about 2.0 mM.

19. The method of claim 18, wherein said divalent ion is cobalt at a concentration of about 0.5 mM to about 1.0 mM.

20. The method of claim 18, wherein said divalent ion is manganese at a concentration of about 0.5 mM to about 1.0 mM.

21. The method of claim 18, wherein one or more of said steps is performed in the presence of divalent magnesium ion at a concentration of about 0.5 mM to about 20 mM.

22. The method of claim 16, wherein said two sets of two probes are oligodeoxyribonucleotide probes, except that at least one of said probes includes at least one ribonucleotide residue.

23. The method of claim 22, further comprising, after the detection step, a step of cleaving ligation products using RNase or alkali.

24. The method of claim 17, further comprising, prior to amplification, a step of cleaving ligation products using RNase.

25. The method of claim 1, wherein said detecting is by means of a hapten marker attached to the outside ends of the primary upstream and secondary downstream probes and by a reporter or different hapten attached to the outside ends of the primary downstream and secondary upstream probes.

26. The method of claim 25 wherein the reporter is a radioactive, fluorescent or chemiluminescent compound.

27. The method of claim 1 wherein the blocking moiety comprises a detectable label and said detecting is by means of monitoring the release of detectable label from the modified probe.

28. The method of claim 2 wherein said upstream probe containing the 3' modification and its complementary probe are selected such that, when the two probes are hybridized together, the 5' terminal residue of the complementary probe lies opposite a nucleotide residue in the upstream probe which is at least one residue 5' to the site of the modification.

29. The method of claim 16 wherein said upstream probe containing the 3' abasic site and its complementary probe are selected such that, when the two probes are hybridized together, the 5' terminal residue of the complementary probe lies opposite a nucleotide residue in the upstream probe which is at least one residue 5' to the abasic site.

30. A diagnostic kit comprising in combination:

(a) two pairs of probes hybridizable with target, wherein at least one of the probes is modified such that, when hybridized, a ligase is substantially incapable of acting on the modified probe as its substrate, the two probes capable of hybridizing to target in positions such that, upon correction of said modified probe, the two probes can be ligated to one another;

(b) a first enzyme reagent having ligase activity for assembling an amplification product; and (c) a second enzyme reagent having endonuclease IV activity capable of correcting the modified probe in a target dependent manner to allow the probe-template complex to be acted upon by the ligase reagent.

31. The kit of claim 30, further including a buffer or means for preparing a buffer containing from 0.05 mM to about 2.0 mM of divalent cobalt ion.

32. The kit of claim 30, further including an RNase reagent or an alkaline reagent.

33. The kit of claim 30 wherein the first enzyme reagent, the second enzyme reagent, or both, are thermostable.

34. The kit of claim 30 wherein the second enzyme reagent comprises Endonuclease IV.

35. A nucleic acid probe having at least three deoxyribonucleotides covalently linked by phosphodiester linkages to define a probe having an available 3' position, the probe further comprising a ribonucleotide attached at the 3' position, the ribonucleotide having a further 3' position to which is attached a group of the formula:

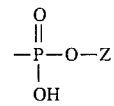

wherein Z is selected from the group consisting of —H; —$(CH_2)_n$CHO, where n is from 1 to about 3; -deoxyribose; and -dideoxyribose.

36. The probe of claim 35 wherein Z is hydrogen.

37. The probe of claim 35 having about 12 to about 50 deoxyribonucleotides.

38. A nucleic acid probe composition comprising a nucleic acid probe according to claim 35 in a buffer.

39. The probe composition of claim 38 wherein Z is hydrogen.

40. The probe composition of claim 38 having about 12 to about 50 deoxyribonucleotides.

* * * * *